US012114843B2

(12) United States Patent
Guo et al.

(10) Patent No.: US 12,114,843 B2
(45) Date of Patent: Oct. 15, 2024

(54) SEALANT APPLICATORS HAVING MIXING AND SPRAYING ASSEMBLIES WITH MALLEABLE SECTIONS AND SPRAY TIPS HAVING REDUCED DIMENSIONS

(71) Applicant: Ethicon, Inc., Somerville, NJ (US)

(72) Inventors: Jianxin Guo, Livingston, NJ (US); Xuelin Guo, Livingston, NJ (US); Joseph LoRicco, Hillsborough, NJ (US); Gwan-Ywan Lai, Princeton Junction, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 17/710,122

(22) Filed: Mar. 31, 2022

(65) Prior Publication Data
US 2023/0309978 A1  Oct. 5, 2023

(51) Int. Cl.
*A61B 17/00* (2006.01)

(52) U.S. Cl.
CPC .......... *A61B 17/00491* (2013.01); *A61B 2017/00495* (2013.01); *A61B 2017/00522* (2013.01)

(58) Field of Classification Search
CPC .... A61B 17/00491; A61B 2017/00495; A61B 2017/00522; A61B 2017/00946
See application file for complete search history.

(56) References Cited

U.S. PATENT DOCUMENTS

| 3,563,373 A | 2/1971 | Paulson |
| 3,923,058 A | 12/1975 | Weingarten |
| 4,059,109 A | 11/1977 | Tischlinger |

(Continued)

FOREIGN PATENT DOCUMENTS

| CN | 102911493 A | 2/2013 |
| CN | 104159626 A | 11/2014 |

(Continued)

OTHER PUBLICATIONS

The Confidence To Know Bleeding Will Stop. Veriset Hemostatic Patch, https://www.medtronic.com/content/dam/covidien/library/emea/en/product/haemostatic-products/weu-veriset-or-guide-lap-open-combined.pdf, 2021, 2 pages, Medtronic.

(Continued)

*Primary Examiner* — Mohamed G Gabr
(74) *Attorney, Agent, or Firm* — Troutman Pepper Hamilton Sanders LLP

(57) ABSTRACT

A mixing and spraying assembly for a tissue sealant includes a mixing assembly, a spray tip assembly, and a malleable section having a proximal end connected with the mixing assembly and a distal end connected with the spray tip assembly for enabling the spray tip assembly to be angulated relative to the mixing assembly. The malleable section includes a flexible shaft having a length, a malleable wire conduit that extends along the length of the flexible shaft, and a malleable wire disposed in the malleable wire conduit. The malleable wire is longer than the flexible shaft and has a proximal end that is connected to the mixing assembly and a distal end that is connected to the spray tip assembly. First and second fluids are mixed within the mixing assembly to form a tissue sealant that is delivered through the malleable section for being expressed from the spray tip assembly.

13 Claims, 17 Drawing Sheets

(56) References Cited

U.S. PATENT DOCUMENTS

| | | | |
|---|---|---|---|
| 4,060,082 A | 11/1977 | Lindberg et al. | |
| 4,424,057 A | 1/1984 | House | |
| 4,631,055 A | 12/1986 | Redl et al. | |
| 4,723,691 A | 2/1988 | Minkevitch et al. | |
| 5,304,165 A | 4/1994 | Haber et al. | |
| 6,224,568 B1 | 5/2001 | Morimoto et al. | |
| 6,458,095 B1* | 10/2002 | Wirt | A61M 11/06 604/82 |
| 6,471,670 B1 | 10/2002 | Enrenfels et al. | |
| 6,475,183 B1 | 11/2002 | Epstein et al. | |
| 6,488,650 B1 | 12/2002 | Epstein et al. | |
| 6,569,113 B2 | 5/2003 | Wirt et al. | |
| 6,575,205 B2 | 6/2003 | Epstein et al. | |
| 6,605,667 B1 | 8/2003 | Badejo et al. | |
| 6,610,033 B1 | 8/2003 | Melanson et al. | |
| 6,699,229 B2 | 3/2004 | Zinger et al. | |
| 7,037,289 B2 | 5/2006 | Dodge et al. | |
| 7,081,103 B2 | 7/2006 | Epstein et al. | |
| 7,021,561 B2 | 8/2006 | Vedrine et al. | |
| 7,207,969 B2 | 4/2007 | Epstein et al. | |
| 7,322,956 B2 | 1/2008 | Fehr et al. | |
| 7,923,031 B2 | 4/2011 | Moller | |
| 7,946,417 B2 | 5/2011 | Plishka et al. | |
| 7,951,108 B2 | 5/2011 | Harper et al. | |
| 7,967,779 B2 | 6/2011 | Bertron et al. | |
| 8,029,468 B2 | 10/2011 | Kriesel et al. | |
| 8,323,262 B2 | 12/2012 | D'Alessio et al. | |
| 8,419,722 B2 | 4/2013 | Richards et al. | |
| 8,821,436 B2 | 9/2014 | Mosler et al. | |
| 9,131,930 B2 | 9/2015 | Greter | |
| 9,398,913 B2 | 7/2016 | Tegels et al. | |
| 9,539,393 B2 | 1/2017 | Johannesson et al. | |
| 9,717,487 B2 | 8/2017 | White et al. | |
| 9,873,098 B2 | 1/2018 | Asada et al. | |
| 10,183,132 B2 | 1/2019 | Wang et al. | |
| 10,420,888 B2 | 9/2019 | Arocha | |
| 10,507,293 B2 | 12/2019 | Goodman et al. | |
| D921,189 S | 6/2021 | Shor et al. | |
| 2001/0016709 A1 | 8/2001 | Tovey et al. | |
| 2003/0040701 A1 | 2/2003 | Dalmose | |
| 2003/0225378 A1 | 12/2003 | Wilkie et al. | |
| 2006/0079834 A1 | 4/2006 | Tennican et al. | |
| 2009/0209916 A1* | 8/2009 | Peindl | A61B 17/00491 604/257 |
| 2010/0219200 A1 | 9/2010 | Plishka et al. | |
| 2011/0178495 A1 | 7/2011 | Ji | |
| 2013/0296822 A1 | 11/2013 | Yokoyama | |
| 2013/0324884 A1 | 12/2013 | Hadvary et al. | |
| 2013/0331658 A1 | 12/2013 | Kai et al. | |
| 2013/0338631 A1 | 12/2013 | Butlin et al. | |
| 2014/0114211 A1 | 4/2014 | Hadvary et al. | |
| 2016/0015900 A1 | 1/2016 | Cronenberg et al. | |
| 2018/0110927 A1 | 4/2018 | Frias Goyenechea et al. | |
| 2018/0117261 A1 | 5/2018 | Steese-Bradley et al. | |
| 2019/0151546 A1 | 5/2019 | Maloney et al. | |
| 2019/0217010 A1 | 7/2019 | Dungar et al. | |
| 2019/0269818 A1 | 9/2019 | Dhanaraj et al. | |
| 2019/0321554 A1 | 10/2019 | Guo et al. | |
| 2020/0360004 A1 | 11/2020 | Guo et al. | |
| 2021/0101162 A1 | 4/2021 | Trezza, II et al. | |
| 2021/0162122 A1 | 6/2021 | Pic et al. | |
| 2022/0133287 A1 | 5/2022 | Addison et al. | |
| 2023/0309977 A1 | 10/2023 | Guo et al. | |

FOREIGN PATENT DOCUMENTS

| | | |
|---|---|---|
| CN | 105194771 A | 12/2015 |
| CN | 108159483 A | 6/2018 |
| CN | 112334077 A | 2/2021 |
| CN | 113521376 A | 10/2021 |
| CN | 113631100 A | 11/2021 |
| EP | 0188981 | 7/1986 |
| EP | 0292472 | 10/1991 |
| EP | 1656214 | 2/2010 |
| EP | 2944277 A1 | 11/2015 |
| JP | 2019171107 | 10/2019 |
| WO | 2001049361 A1 | 7/2001 |
| WO | 2009153042 | 12/2009 |
| WO | 2010134988 A1 | 11/2010 |
| WO | 2012158973 | 11/2012 |
| WO | 2013063396 A1 | 5/2013 |
| WO | 2013134614 A3 | 10/2013 |
| WO | 2016038593 A1 | 3/2016 |
| WO | 2016160469 | 10/2016 |
| WO | 2016038593 A8 | 4/2017 |
| WO | 2018150375 | 8/2018 |
| WO | 2019018198 | 1/2019 |
| WO | 2019077381 | 4/2019 |
| WO | 2019202446 A1 | 10/2019 |
| WO | 2019237080 | 12/2019 |
| WO | 2020197969 A1 | 10/2020 |
| WO | 2021250548 A1 | 12/2021 |
| WO | 2022038439 A1 | 2/2022 |

OTHER PUBLICATIONS

International Search Report and Written Opinion dated Jun. 14, 2023, from corresponding International Patent Application No. PCT/IB2023/052516.

Search Report (English translation) dated Nov. 1, 2023, from corresponding Chinese Patent Application No. 202210756477.7.

Search Report (English translation) dated Nov. 3, 2023, from corresponding Chinese Patent Application No. 202211660674.5.

International Search Report and Written Opinion dated Jun. 20, 2023, from corresponding International Patent Application No. PCT/IB2023/052537.

\* cited by examiner

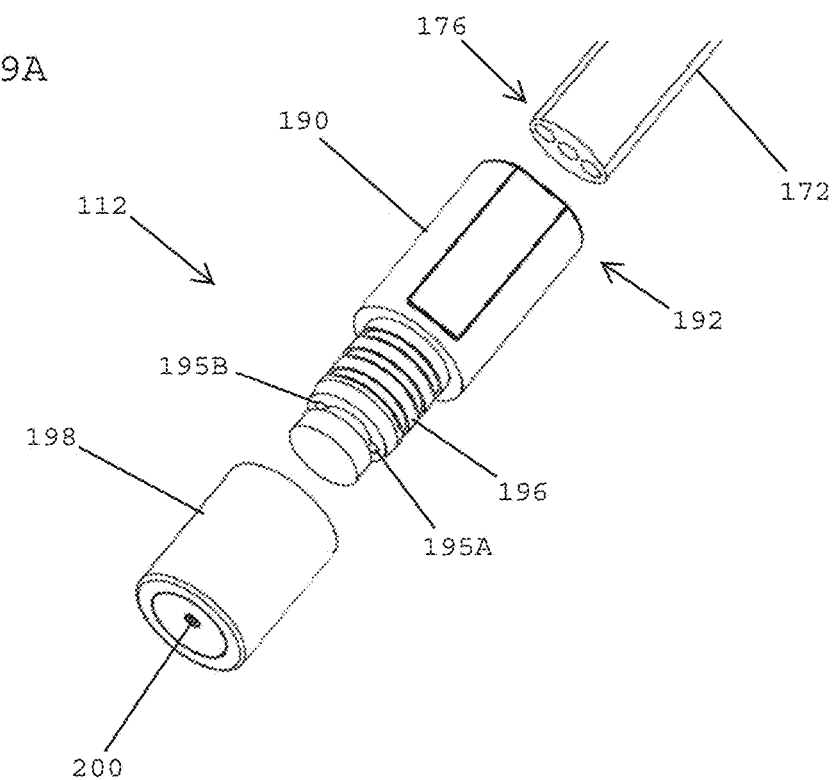
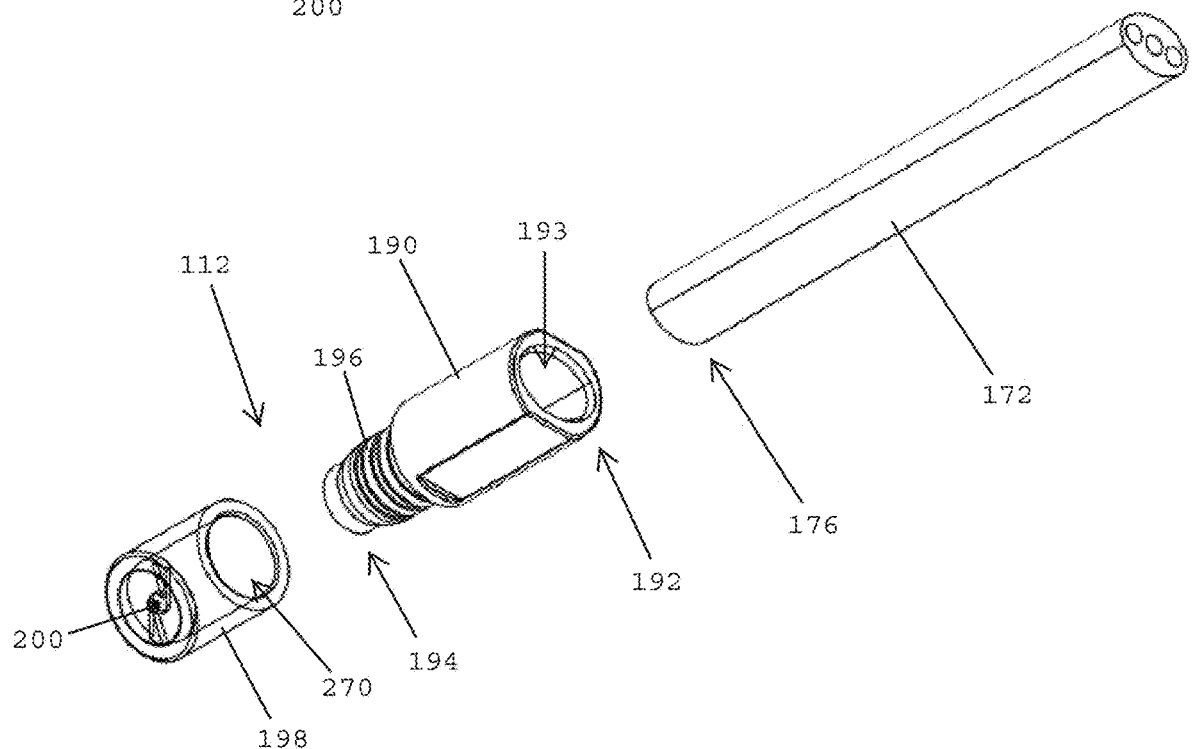

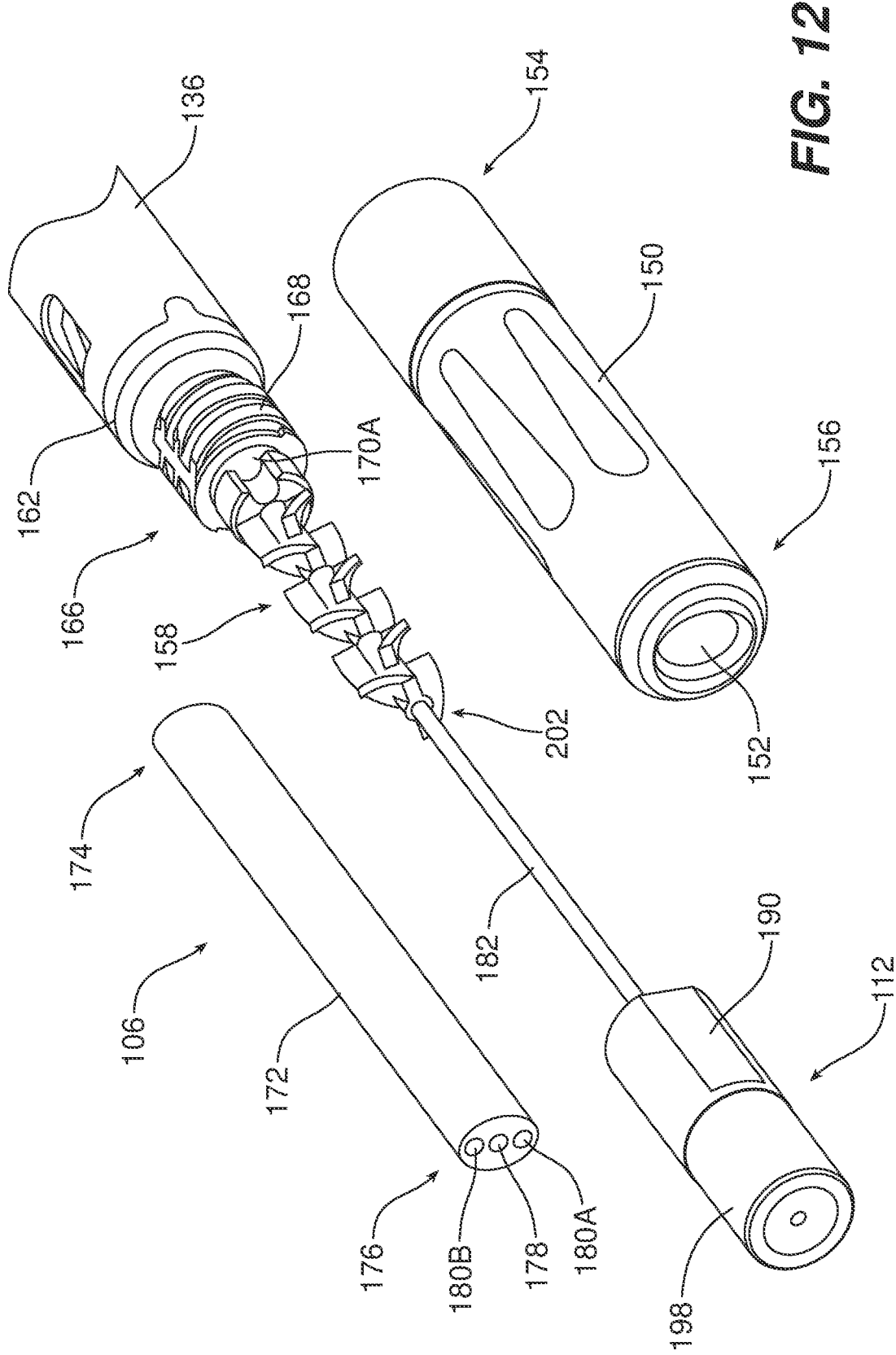

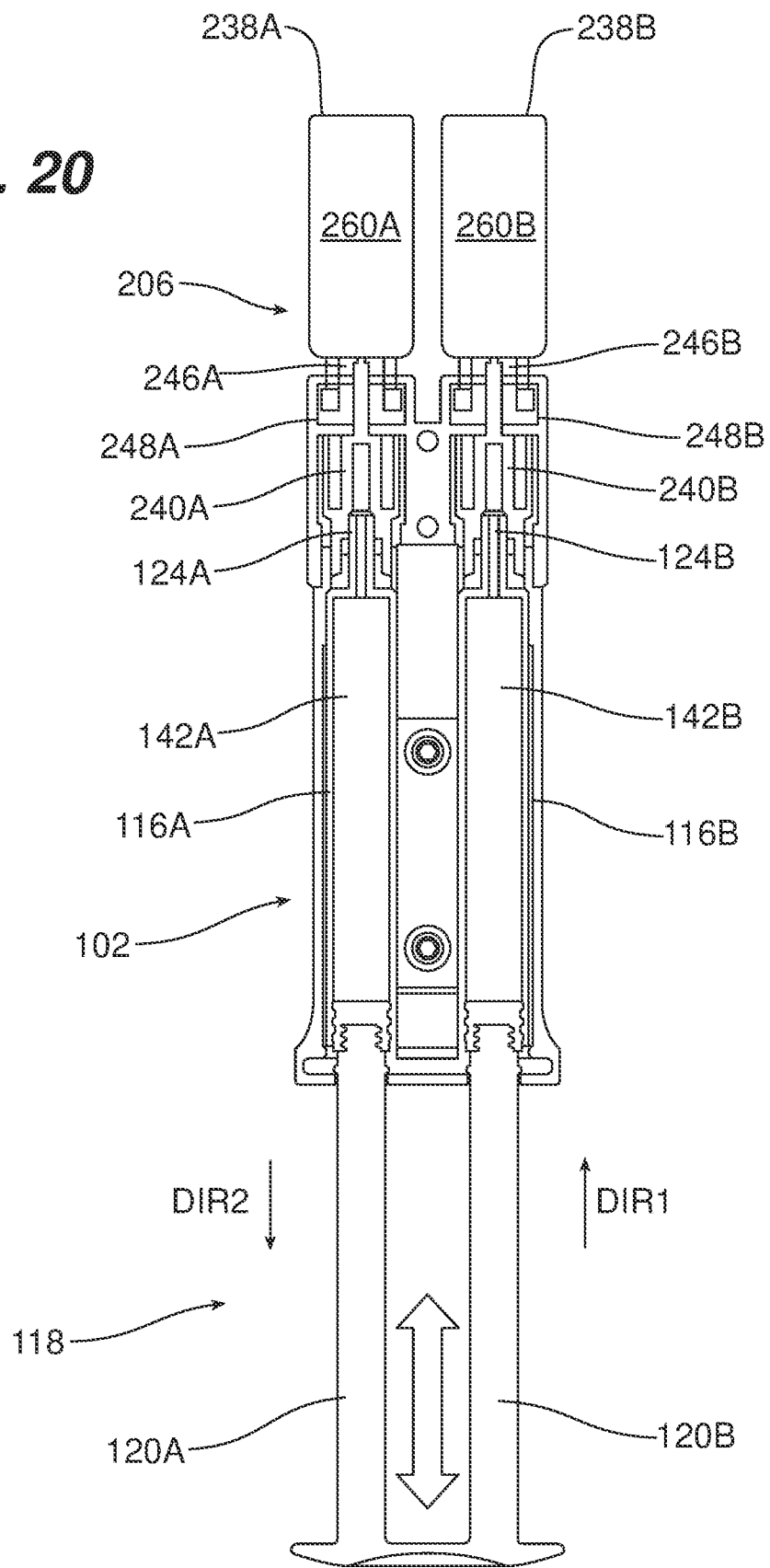

SEALANT APPLICATORS HAVING MIXING AND SPRAYING ASSEMBLIES WITH MALLEABLE SECTIONS AND SPRAY TIPS HAVING REDUCED DIMENSIONS

BACKGROUND OF THE INVENTION

Field of the Invention

The present patent application is related to medical devices and is more particularly related to systems, devices, and methods for expressing tissue sealants and hemostats during surgical procedures.

Description of the Related Art

Mammals can suffer from bleeding due to wounds or during surgical procedures. In some instances, the bleeding is minor and will stop due to normal blood clotting functions or by using simple first aid techniques. In other instances, however, excessive bleeding can occur, which requires the use of specialized equipment and materials, as well as the services of trained personnel in order to administer effective aid.

To address the more challenging circumstances noted above, various materials have been developed for controlling excessive bleeding. For example, topical absorbable hemostats (TAHs) are widely used in surgical applications. TAHs encompass products based on oxidized cellulose (OC), oxidized regenerated cellulose (ORC), gelatin, collagen, chitin, chitosan, starch, etc. To improve the hemostatic performance, scaffolds based on the above materials can be combined with biologically derived clotting factors, such as thrombin and fibrinogen.

Controlling bleeding is essential and critical in surgical procedures to minimize blood loss, shorten the duration of the surgery, and reduce post-surgical complications.

Recently, minimally invasive surgery (MIS) techniques have emerged as an alternative to conventional surgical techniques for performing a wide range of surgical procedures. MIS procedures differ from conventional surgical procedures in that a plurality of devices and/or surgical tools may be introduced into the body through cannulas and/or trocars, which are inserted into small incisions made in the body. As a result of using MIS techniques, trauma to the body is reduced, which decreases recovery time for patients.

One type of minimally invasive surgery involves laparoscopic surgical procedures, which are used to treat hernias, colon dysfunctions, gastroesophageal reflux disease, gallbladder disorders, lung disorders, etc. Typically, a patient undergoing a laparoscopic surgical procedure is able to return home after a short recovery period (e.g., within hours after undergoing surgery).

One challenge presented when performing MIS procedures relates to controlling bleeding at the surgical site. In contrast to conventional open surgical procedures, during a laparoscopic procedure a surgeon's access to a surgical site or surgical cavity is greatly reduced.

In response, tissue sealants and other biological adhesive materials have been developed for use in closing incisions and wounds at surgical sites. Tissue sealants may include fibrin sealants, which comprise thrombin and fibrinogen material, although other formulations are available. Typically, the individual components of the tissue sealants (e.g., thrombin and fibrinogen) are stored separately in isolated reservoirs because the components will rapidly react once they come in contact with one another. In many instances, the two separate components are mixed together for the first time immediately prior to being applied to tissue.

Once mixed, the components coagulate very quickly, yielding an adhesive gel within a short period of time (e.g., within 10-20 seconds).

There have been some developments related to systems for expressing tissue sealants. For example, U.S. Pat. No. 6,458,095 discloses a dispenser for simultaneously dispensing first and second components of an adhesive tissue sealant, wherein at least the first component is stored in the dispenser as dry powder that is dissolved prior to use by introduction of a solvent. The dispenser includes a first container having a first septum at one end, an open end opposite the first septum, and a first movable plug disposed therein. The first container holds a quantity of the first component in the form of a dry powder stored between the first septum and the first movable plug. The dispenser includes a second container having a second septum at one end, an open end opposite the second septum, and a second movable plug disposed therein, the second container containing a quantity of the second component.

U.S. Pat. No. 10,183,132, assigned to Ethicon LLC, the disclosure of which is hereby incorporated by reference herein, teaches an integrated delivery device that is operable with one hand and provides co-delivery of a liquid medicant and a powder medicant onto a tissue or wound from a liquid medicant expression subunit and a powder medicant expression subunit. Each expression subunit has an actuator for the liquid medicant and the powder medicant contained therein, which are positioned near one other at proximal ends of the expression subunits and delivery cannulas for each of the said expression subunits that positioned near one other at distal ends of the expression subunits.

U.S. Pat. No. 10,507,293 to Goodman et al., assigned to Ethicon, Inc. of Somerville, New Jersey, the disclosure of which is hereby incorporated by reference herein, teaches a device for the expression of a hemostatic powder. The device has an elongated reservoir with a manual air pump, such as a bellows, at a proximal end and an expression port at a distal end. A porous filter is slidably disposed within the reservoir between the bellows and plunger and the expression port, and a spring is disposed within the reservoir between the air pump and the plunger. The powder is disposed within the reservoir between the porous filter and the expression port, and the pump is in a fluid communication with the expression port through the porous filter and through the powder.

US 2021/0101162, assigned to Ethicon, Inc., the disclosure of which is hereby incorporated by reference herein, discloses a spray device including a first spray tip having a first fluid pathway defining a first flow area, and a second spray tip includes a second fluid pathway that defines a second flow area that is larger than the first flow area of the first spray tip. The first and second spray tips are side-by-side and spaced from one another at a distal end of the spray device. When a first fluid having a volumetric flow rate is introduced into the first spray tip and a second fluid having the same volumetric flow rate is introduced into the second spray tip, the first fluid will flow through the first fluid pathway at a greater velocity than the second fluid will flow through the second fluid pathway.

In spite of the above advances, there remains a continuing need for improved systems, devices and methods for delivering tissue sealants and hemostats to patients for controlling bleeding. There is also a need for sealant applicators used in minimally invasive surgery that enable tissue sealants and hemostats to be delivered into narrow spaces and small surgical sites inside patients.

SUMMARY OF THE INVENTION

During minimally invasive surgery, there may be a need to apply a tissue sealant within a small, confined space. For example, the thoracic cavity is a small, confined space, which makes it difficult for a conventional spray tip to fit inside the cavity and be far enough away from the lung surface to achieve good spray quality that will effectively seal the lung tissue. In response to these problems, the present patent application discloses a short, malleable spray tip assembly that enables the spray tip to be bent within the small, confined space and still be far enough away from the lung surface to achieve good spray quality.

In one embodiment, a sealant applicator for expressing a tissue sealant or hemostat preferably has a mixing and spraying assembly including a spray tip assembly that is spaced away from a mixing assembly by a malleable section including a flexible shaft that contains a malleable wire. The malleable section enables the spray tip assembly to be angulated relative to the mixing assembly. The spray tip assembly has a shorter length and a smaller outer diameter that enables the spray tip assembly to be positioned within smaller spaces and narrower body cavities for effectively expressing the tissue sealants and hemostats onto tissue.

In one embodiment, a mixing and spraying assembly for a tissue sealant preferably includes a mixing assembly located at a proximal end of the mixing and spraying assembly, a spray tip assembly located at a distal end of the mixing and spraying assembly, and a malleable section having a proximal end connected with the mixing assembly and a distal end connected with the spray tip assembly for enabling the spray tip assembly to be angulated relative to the mixing assembly.

In one embodiment, the malleable section includes a flexible shaft having a proximal end, distal end, and a length that extends between the proximal and distal ends thereof, a malleable wire conduit that extends along the length of the flexible shaft, and a malleable wire disposed in the malleable wire conduit of the flexible shaft.

In one embodiment, the malleable wire has a length that is greater than the length of the flexible shaft. In one embodiment, the malleable wire has a proximal end that extends beyond the proximal end of the flexible shaft and that is connected to the mixing assembly and a distal end that extends beyond the distal end of the flexible shaft and that is connected to the spray tip assembly.

In one embodiment, the mixing assembly includes a mixer housing having a proximal end, a distal end and a mixer housing conduit extending along a length of the mixer housing from the proximal end to the distal end of the mixer housing.

In one embodiment, a mixing element is disposed within the mixer housing conduit. In one embodiment, the proximal end of the malleable wire that extends beyond the proximal end of the flexible shaft is secured to the mixing element.

In one embodiment, the mixing element preferably includes a static mixer having a center shaft that extends along a length of the static mixer, the center shaft having a proximal end and a distal end. In one embodiment, a blind hole may be formed in the center shaft of the static mixer that extends from the distal end of the center shaft toward the proximal end of the center shaft. The blind hold may extend about ⅔ to ¾ of the length of the center shaft of the static mixer.

In one embodiment, the proximal end of the malleable wire may be disposed in the blind hole formed in the center shaft of the static mixer for connecting the proximal end of the malleable wire to the static mixer.

In one embodiment, the mixing assembly may include a proximal connector having a proximal end that is configured for being inserted into an opening at a distal end of an elongated cannula of a sealant applicator and a distal end having external threads.

In one embodiment, the mixer housing preferably has internal threads located at the proximal end of the mixer housing that are configured to mesh with the external threads at the distal end of the proximal connector for securing the mixer housing to the proximal connector.

In one embodiment, the proximal connector may have a first fluid pathway extending from the proximal end to the distal end of the proximal connector, whereby the first fluid pathway is in fluid communication with the proximal end of the static mixer.

In one embodiment, the proximal connector may have a second fluid pathway extending from the proximal end to the distal end of the proximal connector, whereby the second fluid pathway is in fluid communication with the proximal end of the static mixer.

In one embodiment, the first and second fluid pathways that extend through the proximal connector are discrete and/or isolated from one another.

In one embodiment, a first flexible tube may be disposed in the first fluid pathway of the proximal connector for supplying a first fluid to the proximal end of the mixer housing.

In one embodiment, a second flexible tube may be disposed in the second fluid pathway of the proximal connector for supplying a second fluid to the proximal end of the mixer housing.

In one embodiment, the static mixer is adapted for mixing the first and second fluids, whereupon the first and second fluids react together to form a tissue sealant that may be expressed from the spray tip assembly.

In one embodiment, the flexible shaft of the malleable section may have one or more tissue sealant conduits extending along the length thereof for supplying the tissue sealant from the mixing assembly to the spray tip assembly. The tissue sealant preferably flows downstream through the tissue sealant conduits for being supplied to the spray tip assembly.

In one embodiment, the malleable wire conduit extends along a central axis of the flexible shaft, and the one or more tissue sealant conduits of the flexible shaft include first and second tissue sealant conduits that extend along opposite sides of the malleable wire conduit.

In one embodiment, the spray tip assembly may include a distal connector having a proximal end and a distal end having external threads. In one embodiment, the proximal end of the distal connector has a central opening that seats the distal end of the flexible shaft.

In one embodiment, the distal end of the malleable wire that extends beyond the distal end of the flexible shaft is connected with the distal connector.

In one embodiment, the spray tip assembly may include a spray cup having a spray opening for expressing the tissue sealant that is supplied through the first and second tissue sealant conduits of the flexible shaft.

In one embodiment, the spray cup has a tube-shaped proximal end with internal threads that are configured to mesh with the external threads at the distal end of the distal connector for securing the spray cup to the distal connector.

In one embodiment, the distal end of the malleable wire that is secured to the distal connector of the spray tip assembly may have a paddle-shaped flange having a width that is greater than the diameter of a section of the malleable wire that extends to the proximal end of the malleable wire.

In one embodiment, a mixing and spraying assembly for expressing a tissue sealant preferably includes a mixing assembly that is configured for mixing first and second fluids that chemically react together to form a tissue sealant, a spray tip assembly configured for expressing the tissue sealant, and a malleable section having a proximal end connected with the mixing assembly and a distal end connected with the spray tip assembly for enabling the spray tip assembly to be angulated relative to the mixing assembly.

In one embodiment, the malleable section has one or more tissue sealant conduits extending along a length thereof for delivering the tissue sealant from the mixing assembly to the spray tip assembly.

In one embodiment, the malleable section desirably includes a flexible shaft having a malleable wire conduit extending from the proximal end to the distal end thereof, and a malleable wire disposed within the malleable wire conduit.

In one embodiment, the malleable wire preferably has a proximal end that extends beyond the proximal end of the flexible shaft for being connected to the mixing assembly and a distal end that extends beyond the distal end of the flexible shaft for being connected to the spray tip assembly.

In one embodiment, the mixing assembly desirably includes a mixer housing having a proximal end, a distal end, and a mixer housing conduit extending from the proximal end to the distal end of the mixer housing.

In one embodiment, the mixing assembly may include a mixing element disposed within the mixer housing conduit of the mixer housing.

In one embodiment, the spray tip assembly preferably includes a distal connector coupled with the distal end of the flexible shaft and a spray cup having a spray opening secured to a distal end of the distal connector.

In one embodiment, the proximal end of the malleable wire is preferably secured to the mixing element disposed within the mixer housing and the distal end of the malleable wire is preferably secured to the distal connector of the spray tip assembly.

In one embodiment, the mixing element preferably includes a static mixer having a center shaft that extends along a length of the static mixer. In one embodiment, the center shaft of the static mixer having a proximal end and a distal end. In one embodiment, a blind hole is formed in the center shaft of the static mixer that extends from the distal end of the center shaft toward the proximal end of the center shaft. In one embodiment, the proximal end of the malleable wire is disposed in the blind hole formed in the center shaft of the static mixer for connecting the proximal end of the malleable wire to the static mixer.

In one embodiment, the mixer housing has a longitudinal axis that extends from the proximal end to the distal end of the mixer housing. In one embodiment, the malleable section enables the spray tip assembly to be angulated relative to the longitudinal axis of the mixer housing.

In one embodiment, the mixer housing has a first outer diameter, and the spray tip assembly has a second outer diameter that is less than the first outer diameter of the mixer housing.

In one embodiment, a method of expressing a tissue sealant preferably includes obtaining a mixing and spraying assembly including a mixing assembly, a spray tip assembly, and a malleable section having a proximal end connected with the mixing assembly and a distal end connected with the spray tip assembly for spacing the spray tip assembly away from the mixing assembly and for enabling the spray tip assembly to be angulated relative to the mixing assembly.

In one embodiment, the method may include directing first and second fluids into the proximal end of the mixing assembly, and mixing the first and second fluids within the mixing assembly whereupon the first and second fluids react together to form a tissue sealant.

In one embodiment, the method may include passing the tissue sealant through one or more tissue sealant conduits that extend through the malleable section to supply the tissue sealant to the spray tip assembly, and expressing the tissue sealant from a distal end of the spray tip assembly.

In one embodiment, the first fluid may include Fibrinogen and the second fluid may include Thrombin that reacts with the Fibrinogen to form the tissue sealant.

In one embodiment, the malleable section of the mixing and spraying assembly desirably includes a flexible shaft having a malleable wire conduit extending from a proximal end to a distal end thereof, and a malleable wire disposed within the malleable wire conduit. In one embodiment, the malleable wire has a proximal end that extends beyond the proximal end of the flexible shaft and a distal end that extends beyond the distal end of the flexible shaft. In one embodiment, the proximal end of the malleable wire is connected to the mixing assembly and the distal end of the malleable wire is connected to the spray tip assembly.

The systems, devices and methods disclosed herein are not limited to use within thoracic cavities and may be used anywhere on a patient's body to express tissue sealants and/or hemostats.

These and other preferred embodiments of the present patent application will be described in more detail herein.

BRIEF DESCRIPTION OF THE DRAWINGS

FIG. 9A is an exploded view of the spray tip assembly shown in FIG. 7 including distal connector and a spray cup.

FIG. 9B is another exploded view of the spray tip assembly shown in FIG. 9A including the distal connector and the spray cup.

FIG. 12 is a partially assembled view of the mixing and spraying assembly shown in FIGS. 7 and 8.

FIG. 20 illustrates a method of using the syringe assembly and the vial assembly of FIG. 19 for mixing a first fluid with a first powder and a second fluid with a second powder, in accordance with one embodiment of the present patent application.

DETAILED DESCRIPTION OF PREFERRED EMBODIMENTS

Figure 1:
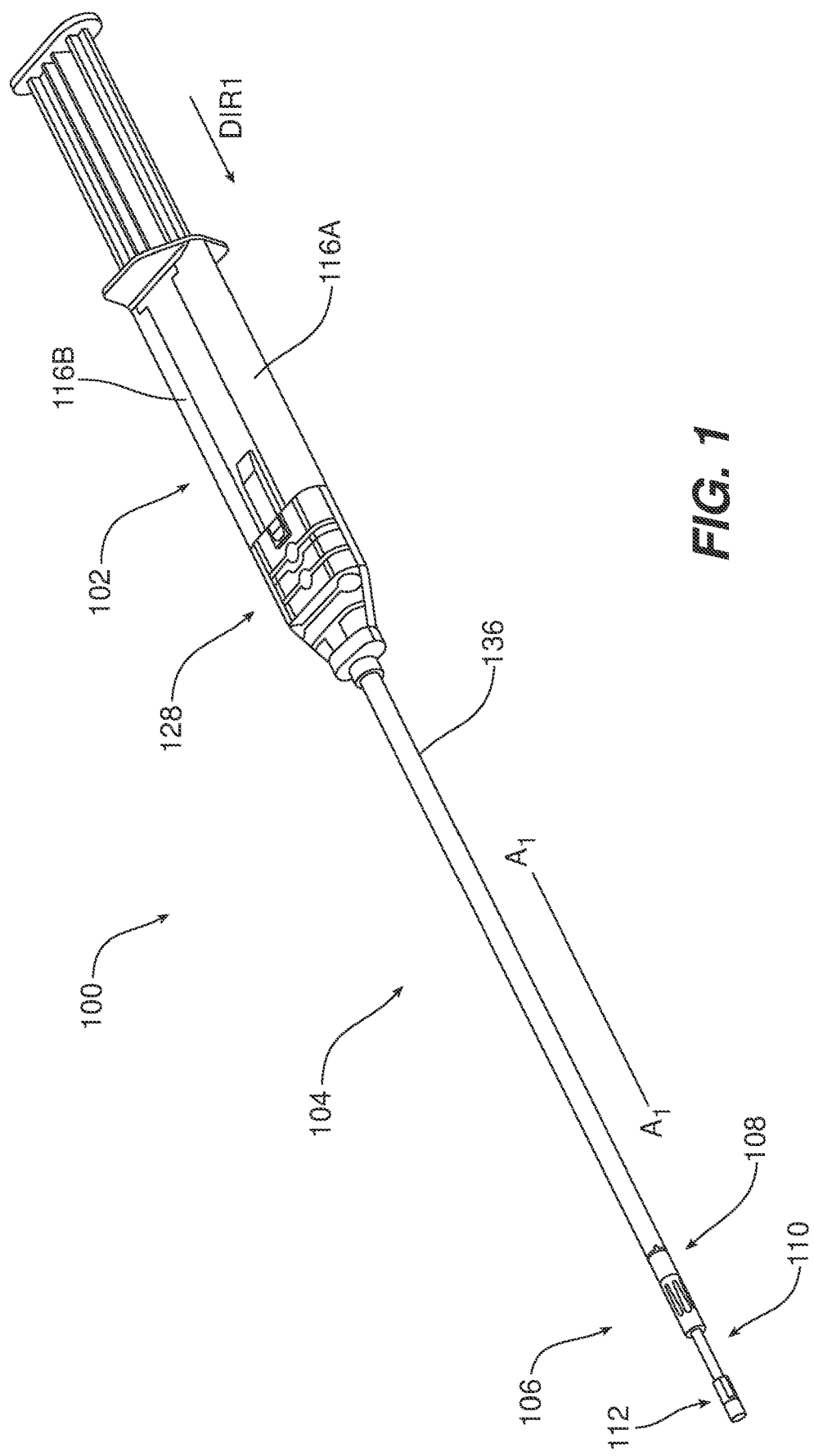
FIG. 1 is a perspective of a sealant applicator including a syringe assembly, a sealant delivery assembly, and a mixing and spraying assembly, in accordance with one embodiment of the present patent application.

FIG. 1, in one embodiment, a sealant applicator 100 for expressing a tissue sealant and/or hemostat during a surgical procedure preferably includes a syringe assembly 102, a sealant delivery assembly 104, and a mixing and spraying assembly 106. In one embodiment, the sealant delivery assembly 104 is secured to a distal end of the syringe assembly 102, and the mixing and spraying assembly 106 is secured to a distal end of the sealant delivery assembly 104.

In one embodiment, the mixing and spraying assembly 106 preferably includes a mixing assembly 108, a malleable section 110, and a spray tip assembly 112. The malleable section 110 preferably interconnects a distal end of the mixing assembly 108 and a proximal end of the spray tip assembly 112 for enabling the spray tip assembly 112 to be angulated and/or oriented at different angles relative to a longitudinal axis $A_1$ of an elongated cannula of the sealant delivery assembly 104.

Figure 2:
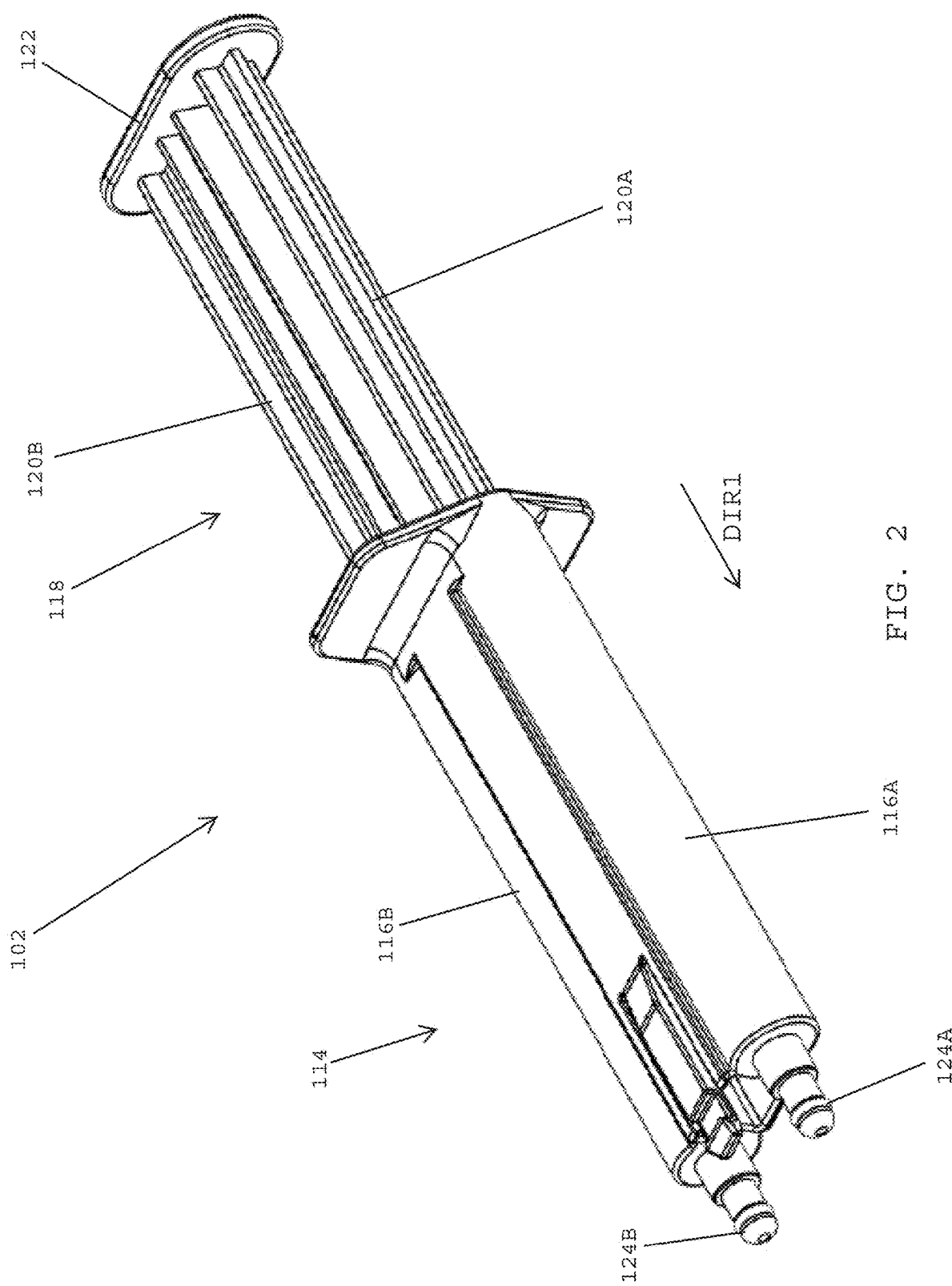
FIG. 2 is a perspective of the syringe assembly shown in FIG. 1.

Referring to FIG. 2, in one embodiment, the syringe assembly 102 of the sealant applicator 100 (FIG. 1) preferably includes a double barrel syringe 114 having a first syringe barrel 116A that is adapted to receive a first fluid and a second syringe barrel 116B that is adapted to receive a second fluid that is mixed with the first fluid for forming a tissue sealant. In one embodiment, the syringe assembly 102 preferably includes a dual barrel plunger 118 including a first plunger rod 120A that is insertable into the first syringe barrel 116A and a second plunger rod 120B that is insertable into the second syringe barrel 116B. The syringe assembly 102 preferably includes a tab 122 (e.g., a thumb tab) that interconnects proximal ends of the first and second plunger rods 120A, 120B.

In one embodiment, the syringe assembly 102 preferably includes a first dispensing tip 124A located at a distal end of the first syringe barrel 116A and a second dispensing tip 124B located at a distal end of the second syringe barrel 116B.

In one embodiment, a first fluid (e.g., a first sealant precursor; an activation fluid; a buffer solution) may be disposed within a first fluid chamber of the first syringe barrel 116A and a second fluid (e.g., a second sealant precursor; an activation fluid; a buffer solution) may be disposed within a second fluid chamber of the second syringe barrel 116B. In one embodiment, the tab 122 may be depressed in the distal direction DIR1 for forcing the first and second fluids to be dispensed via the respective first and second dispensing tips 124A, 124B located at the distal ends of the first and second syringe barrels 116A, 116B.

In one embodiment, the first and second fluids may be first and second tissue sealant precursors that are mixed together to form a tissue sealant or hemostat, which may be expressed from a distal end of the sealant applicator 100. In one embodiment, the first and second fluids preferably react when mixed with one another to form a tissue sealant or hemostat. In one embodiment, the first and second fluids are preferably isolated from one another until being directed into the mixing and spraying assembly 106 (FIG. 1), whereupon the first and second fluids are mixed together and expressed from the spray tip assembly 112 (FIG. 1) that is located at the distal end of the sealant applicator.

Figure 3:
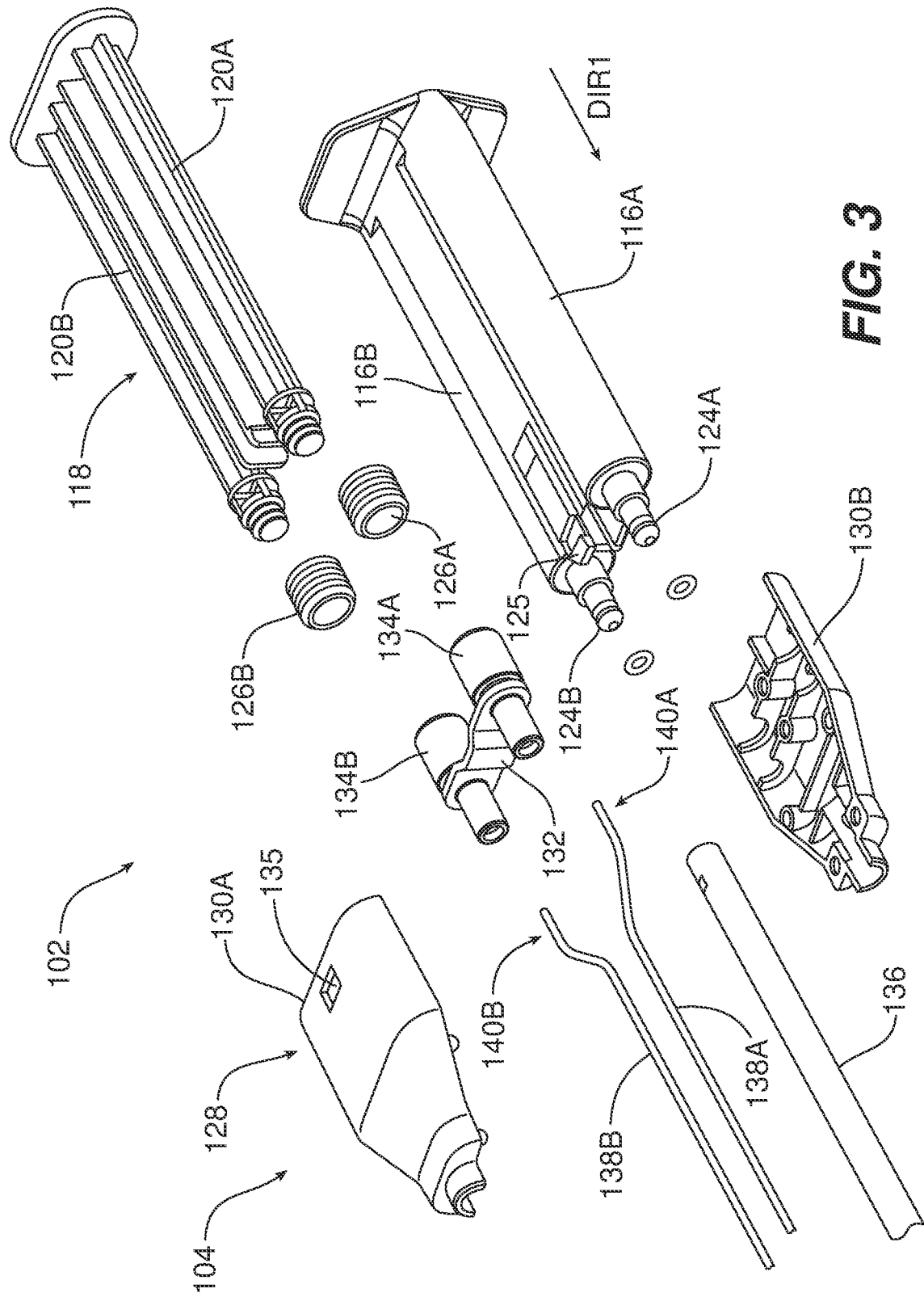
FIG. 3 is an exploded view of the syringe assembly and a proximal end of the sealant delivery assembly shown in FIG. 1.

Referring to FIG. 3, in one embodiment, the syringe assembly 102 preferably includes a first plunger 126A securable to a distal end of the first plunger rod 120A and a second plunger 126B securable to a distal end of the second plunger rod 120B. In one embodiment, the outer perimeter of the first plunger 126B preferably forms a fluid-tight seal with an inner surface of the first syringe barrel 116A, and the outer perimeter of the second plunger 126B preferably forms a fluid-tight seal with an inner surface of the second syringe barrel 116B. When the dual barrel plunger 118 is moved in the distal direction DIR1 relative to the first and second syringe barrels 116A, 116B, the first plunger 126A forces the first fluid from the first dispensing tip 124A and the second plunger 126B forces the second fluid from the second dispensing tip 124B.

In one embodiment, the sealant delivery assembly 104 (FIG. 1) preferably includes a sealant delivery housing 128 having a first housing part 130A and a second housing part 130B. In one embodiment, the first and second housing parts 130A, 130B of the sealant delivery housing 128 may be snap-fit together. In one embodiment, the sealant delivery housing is adapted for being secured to the distal end of the syringe assembly 102. In one embodiment, the distal end of the syringe assembly 102 desirably includes a latching mechanism 135 that is configured to engage a latch opening 135 formed in the first housing part 130A of the sealant delivery housing 128. In one embodiment, the latching mechanism 135 is moveable between a first position (e.g., an extended position) for locking the sealant delivery housing to the distal end of the syringe assembly and a second position (e.g., a depressed position) for releasing the sealant delivery housing from its attachment to the distal end of the syringe assembly 102.

In one embodiment, the sealant delivery assembly 104 preferably includes a connector 132 that interconnects a first hub 134A (e.g., a first fluid port) and second hub 134B (e.g., a second fluid port). In one embodiment, when the proximal end of the sealant delivery assembly 104 is coupled with a distal end of the syringe assembly 102, the first dispensing tip 124A of the first syringe barrel 116A is preferably inserted into the first hub 134A, and the second dispensing tip 124B of the second syringe barrel 116B is inserted into the second hub 134B for providing fluid communication between the first and second syringe barrels and the respective first and second hubs 134A, 134B.

In one embodiment, the sealant delivery assembly 104 preferably includes an elongated cannula 136 (e.g., an elongated tubular shaft) that preferably extends between proximal and distal ends of the sealant delivery assembly. The elongated cannula 136 may be rigid. In one embodiment, first and second flexible tubes 138A, 138B are disposed within the elongated cannula 136 for delivery the first and second fluids to the mixing and spraying assembly 106 located that the distal end of the sealant applicator 100 (FIG. 1). In one embodiment, a proximal end 140A of the first flexible tube 138A is preferably in fluid communication with a distal end of the first hub 134A, and a proximal end 140B of the second flexible tube 138B is preferably in fluid communication with a distal end of the second hub 134B. In one embodiment, the first fluid that is supplied from the first syringe barrel 116A preferably passes through the first flexible tube 138A and the second fluid supplied from the second syringe barrel 116B preferably passes through the second flexible tube 138B.

Figure 4A:
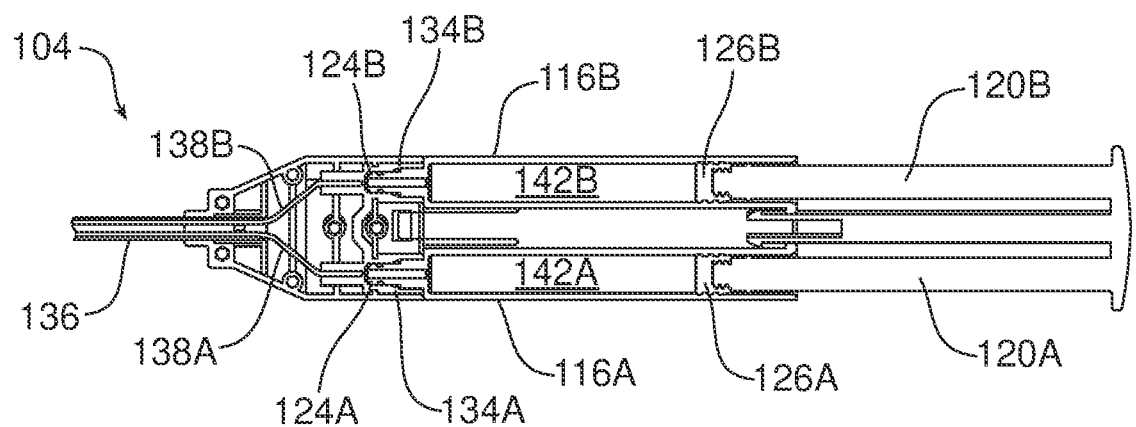
FIG. 4A is a cross-sectional view of the syringe assembly and the proximal end of the sealant delivery assembly shown in FIG. 1.
Figure 4B:
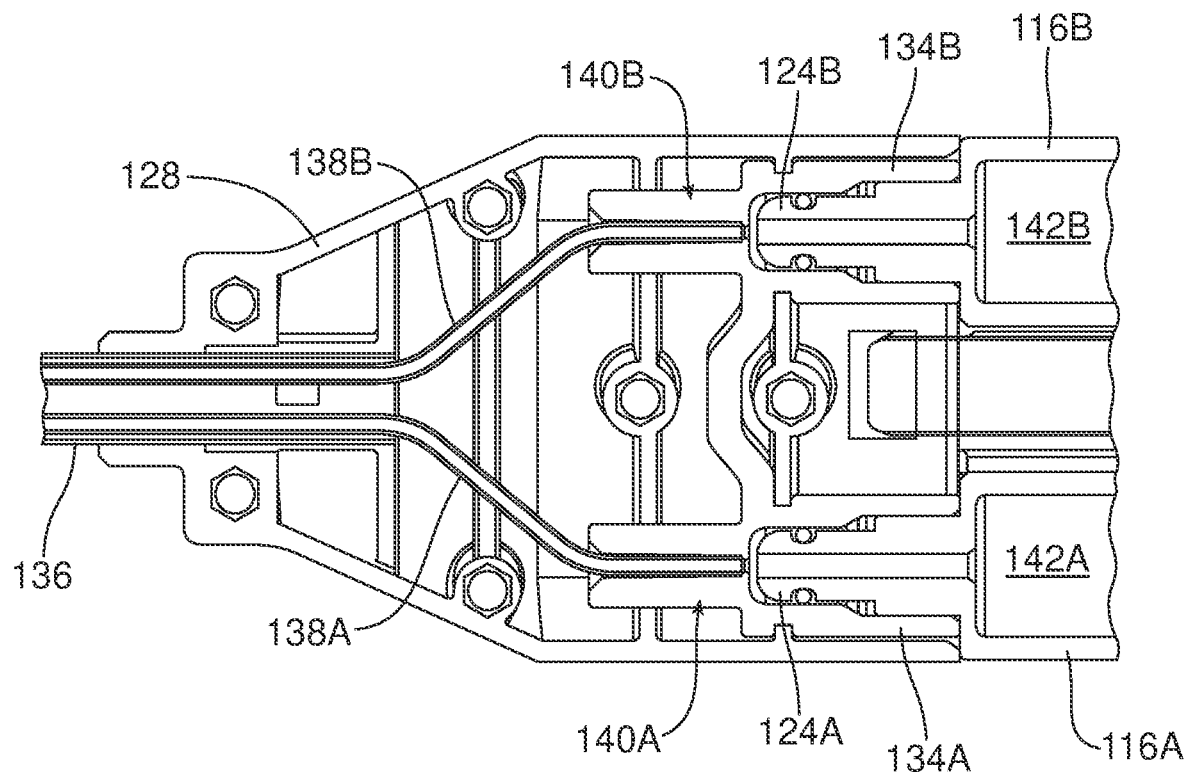
FIG. 4B is a magnified view of a distal end of the syringe assembly and the proximal end of the sealant delivery assembly shown in FIG. 4A.

Referring to FIGS. 4A and 4B, in one embodiment, the proximal end of the sealant delivery assembly 104 is configured for being connected with a distal end of the syringe assembly 102. The syringe assembly 102 preferably includes the first and second syringe barrels 116A, 116B. The first plunger 126A and a distal end of the first plunger rod 120A are preferably inserted into a proximal end of a first fluid chamber 142A of the first syringe barrel 116A for forcing the first fluid from the first dispensing tip 124A of the first syringe barrel 116A. The second plunger 126B and a distal end of the second plunger rod 120B are preferably inserted into a proximal of a second fluid chamber 142B of the second syringe barrel 116B for forcing the second fluid from the second dispensing tip 124B of the second syringe barrel 116B.

In one embodiment, the first dispensing tip 124A located at the distal end of the first syringe barrel 116A is preferably inserted into the first hub 134A, and the second dispensing tip 124B located at the distal end of the second syringe barrel 116B is preferably inserted into the second hub 134B.

In one embodiment, the proximal end 140A of the first flexible tube 138A is inserted into a distal end of the first hub 134A for providing fluid communication between the first fluid chamber 142A of the first syringe barrel 116A and the first flexible tube 138A. In one embodiment, the proximal end 140B of the second flexible tube 138B is inserted into a distal end of the second hub 134B for providing fluid communication between the second fluid chamber 142B of the second syringe barrel 116B and the second flexible tube 138B.

The first and second flexible tubes 138A, 138B are disposed within the elongated cannula 136 that extends between a distal end of the sealant delivery housing 128 and the mixing and spraying assembly 106 located at a distal end of the sealant applicator 100 (FIG. 1).

Figure 5:
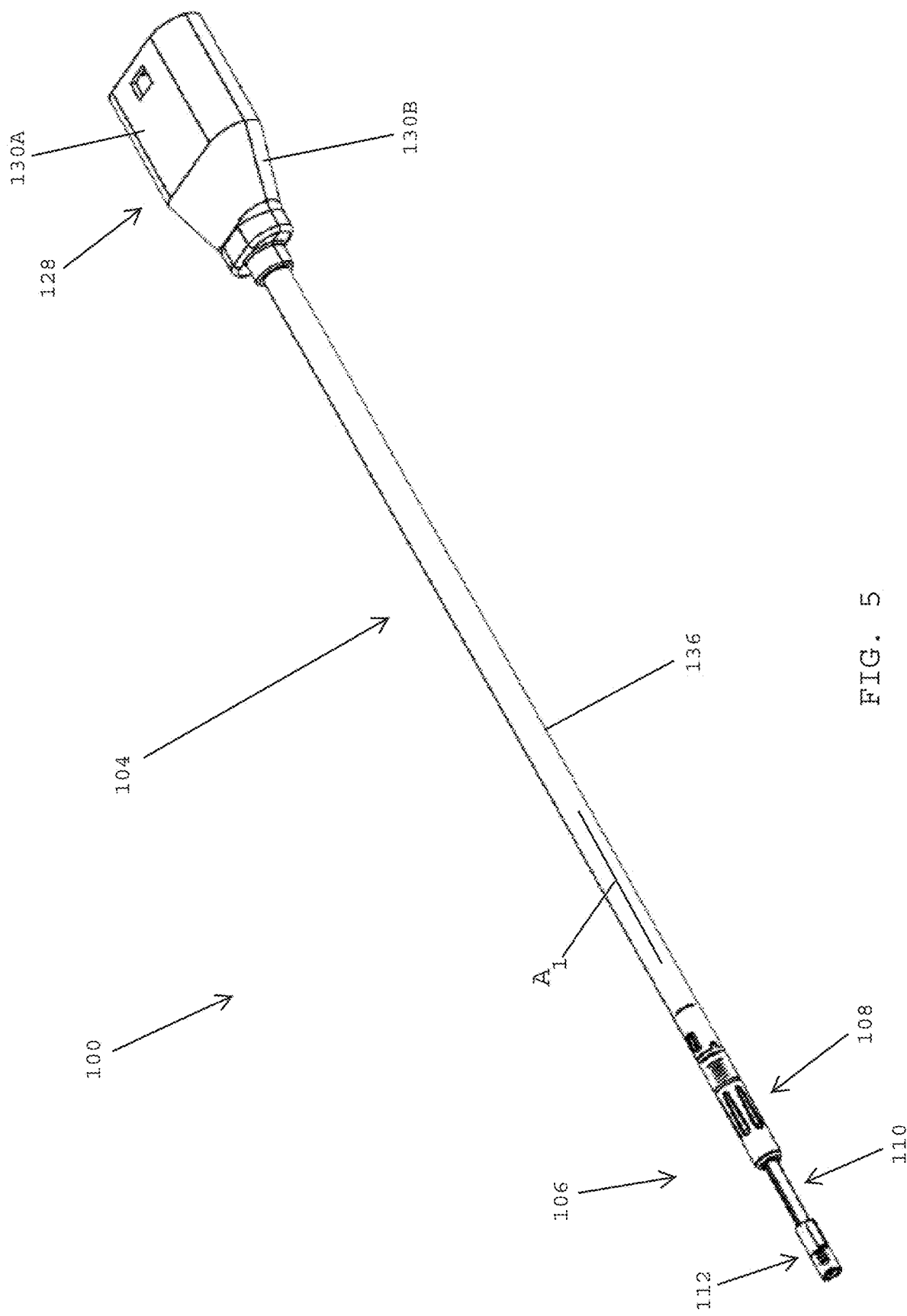
FIG. 5 is a perspective view of the sealant delivery assembly and the mixing and spraying assembly shown in FIG. 1.

Referring to FIG. 5, in one embodiment, the sealant applicator 100 preferably includes the sealant delivery assembly 104 and the mixing and spraying assembly 106 connected with a distal end of the elongated cannula 136 of the sealant delivery assembly 104. In one embodiment, the sealant delivery assembly 104 preferably includes the sealant delivery housing 128 having a first housing part 130A and a second housing part 130B that are preferably snap-fit together. The elongated cannula 136 has a proximal end connected with the sealant delivery housing 128 and a distal end connected with the mixing and spraying assembly 106. The elongated cannula 136 is preferably rigid and extends along a longitudinal axis $A_1$. In one embodiment, the elongated cannula 136 may be a hollow tube made of biocompatible material such as metal (e.g., stainless steel) or polymers.

In one embodiment, the mixing and spraying assembly 106 preferably includes a mixing assembly 108, a malleable section 110, and a spray tip assembly 112. In one embodiment, the malleable section 110 enables the spray tip assembly 112 to be angulated relative to the mixing assembly 108 and/or the longitudinal axis $A_1$ of the elongated cannula 136. The malleable section 110 may contain a malleable wire having shape memory properties for enabling the spray tip assembly 112 to be angulated relative to a longitudinal axis of the mixing assembly 108 and/or the elongated cannula 136.

Figure 6:
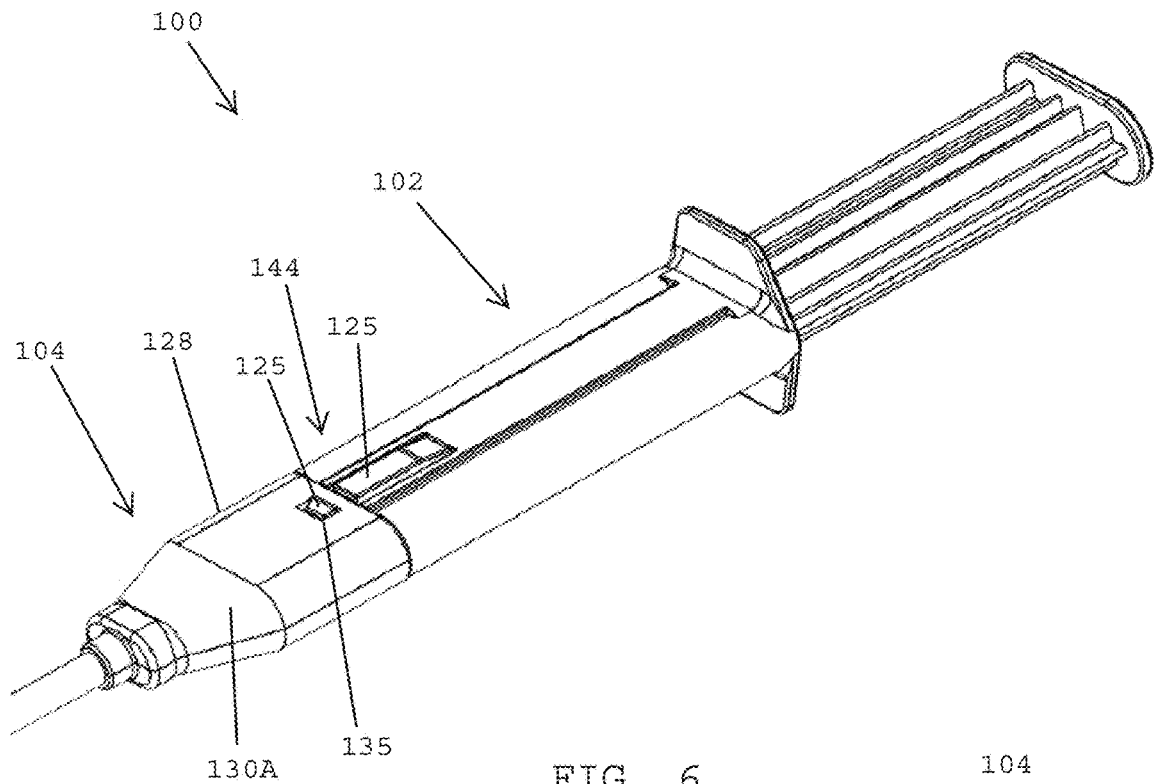
FIG. 6 is a perspective view of the syringe assembly and the proximal end of the sealant delivery assembly shown in FIG. 1.

Referring to FIG. 6, in one embodiment, a proximal end of the sealant applicator 100 preferably includes the syringe assembly 102 and the sealant delivery assembly 104. In one embodiment, the syringe assembly 102 preferably includes a locking assembly 144 including the resilient latch 125 that engages the latch opening 135 formed in the first part 130A of the sealant delivery housing 128 for selectively locking the sealant assembly housing 128 to the distal end of the syringe assembly 102. In one embodiment, the locking assembly 144 may be depressed for uncoupling the resilient latch 125 from the latch opening 135 so that the sealant delivery assembly 104 may be disconnected from being secured to the distal end of the syringe assembly 102.

Figure 7:
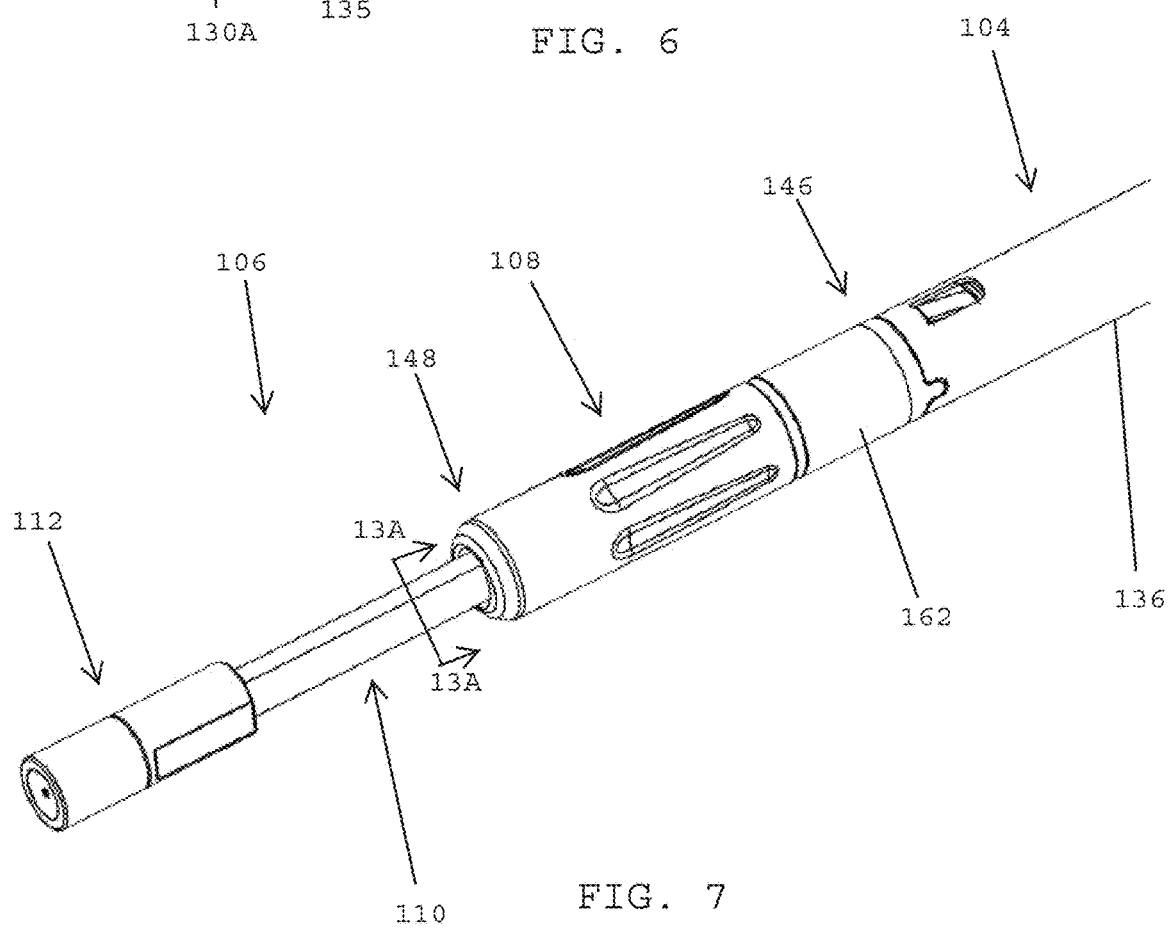
FIG. 7 is a perspective view of the mixing and spraying assembly located at a distal end of the sealant applicator shown in FIG. 1, the mixing and spraying assembly including a mixing assembly, a malleable section, and a spray tip assembly.

Referring to FIG. 7, in one embodiment, the mixing and spraying assembly 106 is preferably secured to a distal end of the elongated conduit 136 of the sealant delivery assembly 104. The mixing and spraying assembly 106 preferably includes the mixing assembly 108, the malleable section 110, and the spray tip assembly 112 that is connected to a distal end of the malleable section 110. In one embodiment, the first and second fluids that are delivered by the sealant delivery assembly 104 are directed into a proximal end 146 of the mixing assembly 108. The first and second fluids are desirably mixed together within the mixing assembly 108 as the first and second fluids flow downstream between the proximal end 146 and a distal end 148 of the mixing assembly 108. The malleable section 110 is located distal (i.e., downstream) to the distal end 148 of the mixing assembly 108, and proximal (i.e., upstream) to the proximal end of the spray tip assembly 112. Thus, the malleable section 110 spaces the spray tip assembly 112 away from the mixing assembly 108.

Figure 8:
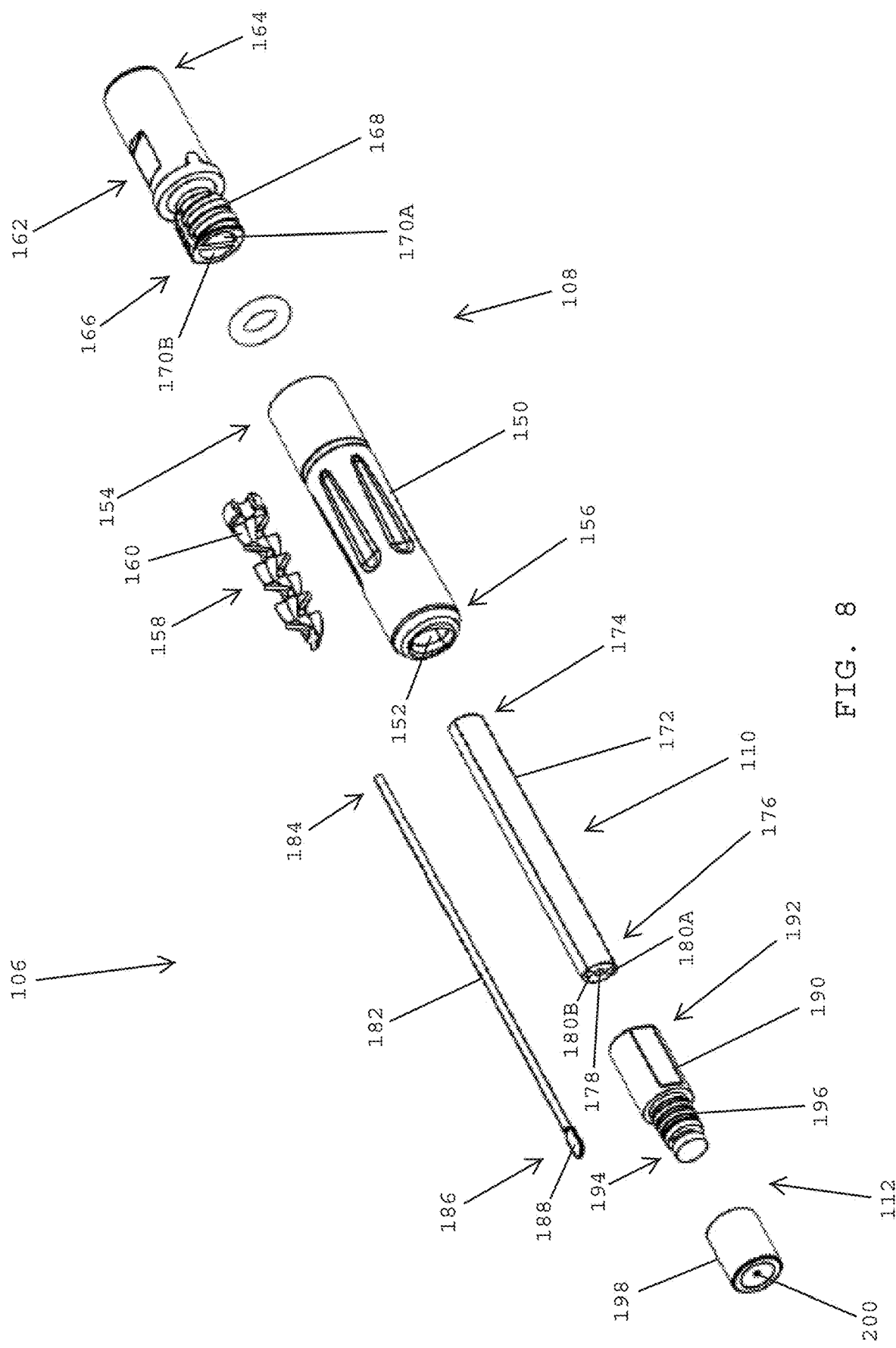
FIG. 8 is an exploded view of the mixing and spraying assembly shown in FIG. 7.

Referring to FIG. 8, in one embodiment, the mixing and spraying assembly 106 preferably includes the mixing assembly 108, the malleable section 110, and the spray tip assembly 112. The mixing assembly 108 preferably includes a mixer housing 150 having an elongated conduit 152 extending from a proximal end 154 to a distal end 156 of the mixer housing 150. In one embodiment, the mixing assembly 108 preferably includes a mixing element 158 (e.g., a static mixer) that is disposed within the elongated conduit 152 of the mixer housing 150. In one embodiment, the mixing element 158 preferably includes a plurality of mixing fins 160 that are spaced from one another along the length of the mixing element 158. The mixing element 158 is configured for mixing the first and second fluids together as the first and second fluids flow through the mixer housing 150.

In one embodiment, the mixing assembly 108 preferably includes a proximal connector 162 (FIG. 7) having a proximal end 164 that is insertable into a distal end of the elongated cannula 136 (FIG. 7) and a distal end 166 having external threads 168 that are adapted to mesh with internal threads (not shown) located at the proximal end 154 of the mixer housing 150. The proximal connector 162 has a first fluid pathway 170A that is in fluid communication with the first flexible tube 138A (FIG. 4B) and a second fluid pathway 170B that is in fluid communication with the second flexible tube 138B (FIG. 4B). The first and second fluid pathways are preferably discrete and/or isolated from one another as they pass through the length of the proximal connector. The first and second fluid pathways 170A, 170B preferably direct the first and second fluids into the proximal end 154 of the mixer housing 150, whereupon the first and second fluids are mixed together by the mixing fins 160 of the mixing element 158.

In one embodiment, the malleable section 110 of the mixing and spraying assembly 106 preferably includes a flexible shaft 172 (e.g., a flexible tube; a flexible member) having a proximal end 174 and a distal end 176. The flexible shaft may be made of a polymer material (e.g., rubber). The flexible shaft 172 desirably has a malleable wire opening 178 and first and second tissue sealant openings 180A, 180B that extend along the length of the flexible shaft 172. In one embodiment, the malleable section 110 preferably includes a malleable wire 182 that is configured to extend through the malleable wire opening 178 of the flexible shaft 172. The malleable wire 182 preferably has a proximal end 184 that is configured for being connected with the mixing element 158 and a distal end 186 including a paddle-shaped flange 188 that has a width that is greater than the outer diameter of the malleable wire 182 that extends in a proximal direction from the paddle-shaped flange 188.

Referring to FIGS. 8 and 9A-9B, in one embodiment, the spray tip assembly 112 of the mixing and spraying assembly 106 preferably includes a distal connector 190 having a proximal end 192 and a distal end 194 having external threads 196. In one embodiment, the proximal end 192 of the distal connector 190 is preferably configured to receive the distal end 176 of the flexible shaft 172 and the distal end 186 of the malleable pin 182.

In one embodiment, the spray tip assembly 112 of the mixing and spraying assembly 106 desirably includes a spray cup 198 having a spray opening 200. The spray cup 198 preferably has internal threads (not shown) that mesh with the external threads 196 at the distal end 194 of the distal connector 190 for securing the spray cup 198 to the distal connector 190.

Figure 10:
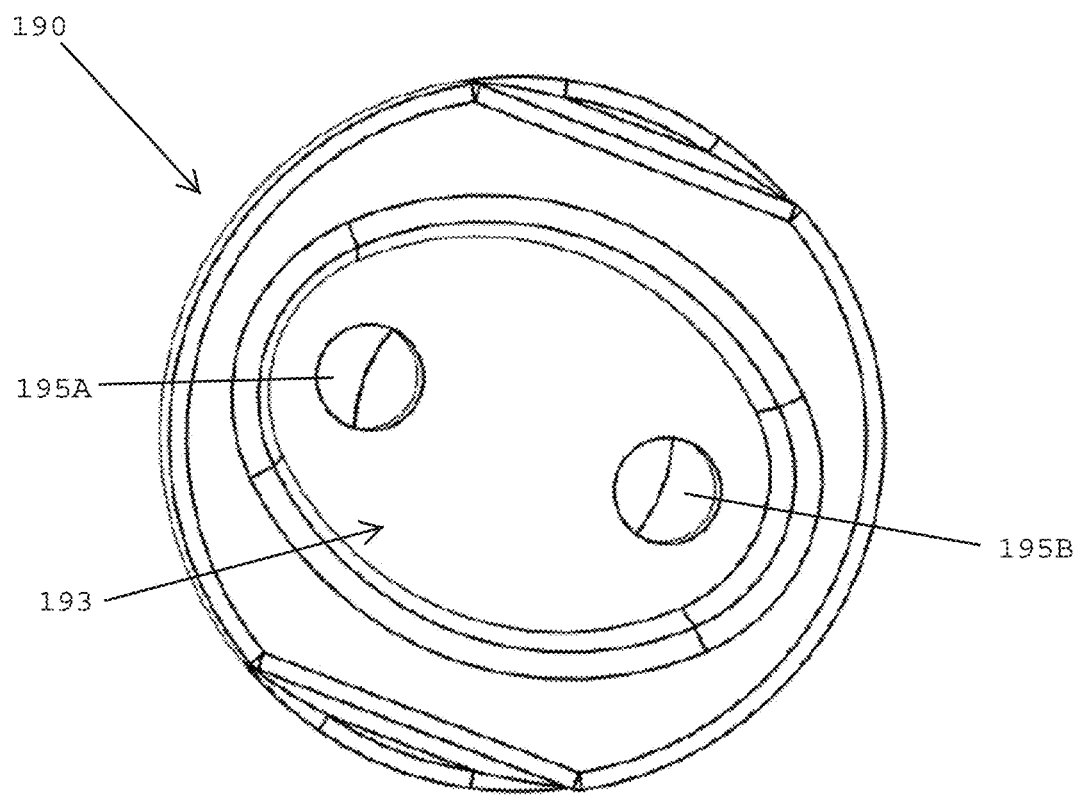
FIG. 10 is a proximal end view of the distal connector shown in FIGS. 9A and 9B.

Referring to FIGS. 9B and 10, in one embodiment, the proximal end 192 of the distal connector 190 has a proximal opening 193 that is adapted to receive the distal end 176 of the flexible shaft 172. The distal connector 190 preferably includes first and second tissue sealant openings 195A, 195B that direct the tissue sealant into the proximal end of the spray cup 198 for being expressed via the spray opening 200 of the spray cup 198.

Figure 11:
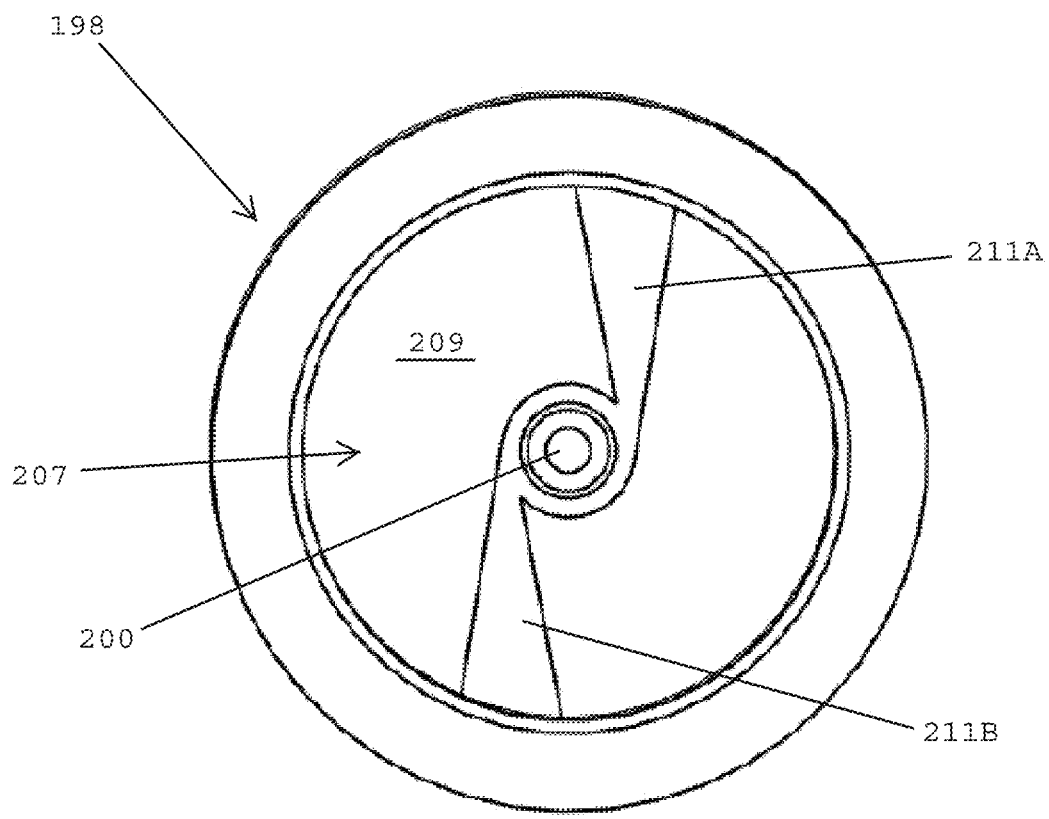
FIG. 11 is a proximal end view of the spray cup shown in FIGS. 9A and 9B.

Referring to FIGS. 9B and 11, in one embodiment, the spray cup 198 has a proximal end with a proximal opening 207 that is preferably adapted to receive the external threads 196 located at the distal end of the distal connector 190. In one embodiment, the spray cup 198 preferably has a closed distal end wall 209 that has the spray opening 200 formed therein for expressing the tissue sealant that passes through the distal connector 190. The distal end wall 209 has flutes 211A, 21B formed therein that direct the tissue sealant into a swirl chamber 215 that surrounds the spray opening 200 as disclosed in commonly assigned U.S. patent application Ser. No. 16/593,799, filed on Oct. 4, 2019, published as US 2021/0101162 on Apr. 8, 2021, the disclosure of which is hereby incorporated by reference herein.

Referring to FIG. 12, in one embodiment, the proximal connector 162 of the mixing and spraying assembly 106 is preferably inserted into an opening at a distal end of the elongated cannula 136 of the sealant delivery assembly. The distal end 166 of the proximal connector 162 has external threads 168 that preferably mesh with internal threads (not shown) located at the proximal end 154 of the mixer housing 150. The mixing element 158 is located downstream of the first and second fluid conduits 170A, 170B that are accessible at the distal end 166 of the proximal connector 162. The proximal end 184 (FIG. 8) of the malleable wire 182 that passes through the flexible shaft 172 is inserted into a blind hole 202 formed in a center shaft of the mixing element 158. The blind hole 202 of the mixing element 158 preferably extends along a longitudinal axis of the center shaft of the mixing element 158. In one embodiment, the blind hole 202 may extend up to about ½ to ¾ of the length of the center shaft of the mixing element and the proximal end of the malleable wire may be fully inserted into the blind hole 202 to ensure a secure connection between the mixing element and the proximal end of the malleable wire.

In one embodiment, the flexible shaft 172 of the malleable section 110 (FIG. 1) has the malleable wire conduit 178 that is adapted to receive the malleable wire 182. The malleable wire conduit 178 that receives the malleable wire preferably extends along the length of the flexible shaft between the proximal end 174 and the distal end 176 thereof. The flexible shaft 172 preferably includes the first and second tissue sealant conduits 180A, 180B that extend along the length of the flexible shaft 172. After the first and second fluids have been mixed together within the mixer housing 150, the first and second tissue sealant conduits 180A, 180B preferably deliver the mixture of the first and second fluids (i.e., the flowable tissue sealant) to the spray tip assembly 112 for being expressed from the distal end of the mixing and spraying assembly 106 (FIG. 1).

In one embodiment, the mixer housing 150 preferably includes the elongated conduit 152 that extends along the length of the mixer housing 150. The mixing element 158 (e.g., a static mixer) is preferably disposed within the elongated conduit 152 of the mixer housing 150. The proximal end 174B of the flexible shaft 172 and the proximal end of the malleable wire 182 are preferably disposed within the elongated conduit 152 at the proximal end 156 of the mixer housing 150.

The paddle-shaped flange 188 at the distal end 186 (FIG. 8) of the malleable wire 182 is preferably connected with the distal connector 190 for coupling the distal connector 190 with the malleable wire 182 and the flexible shaft 172. The spray cup 198 is preferably threaded onto the external threads 196 (FIG. 9A) located at the distal end of the distal connector 190.

Figure 13A:
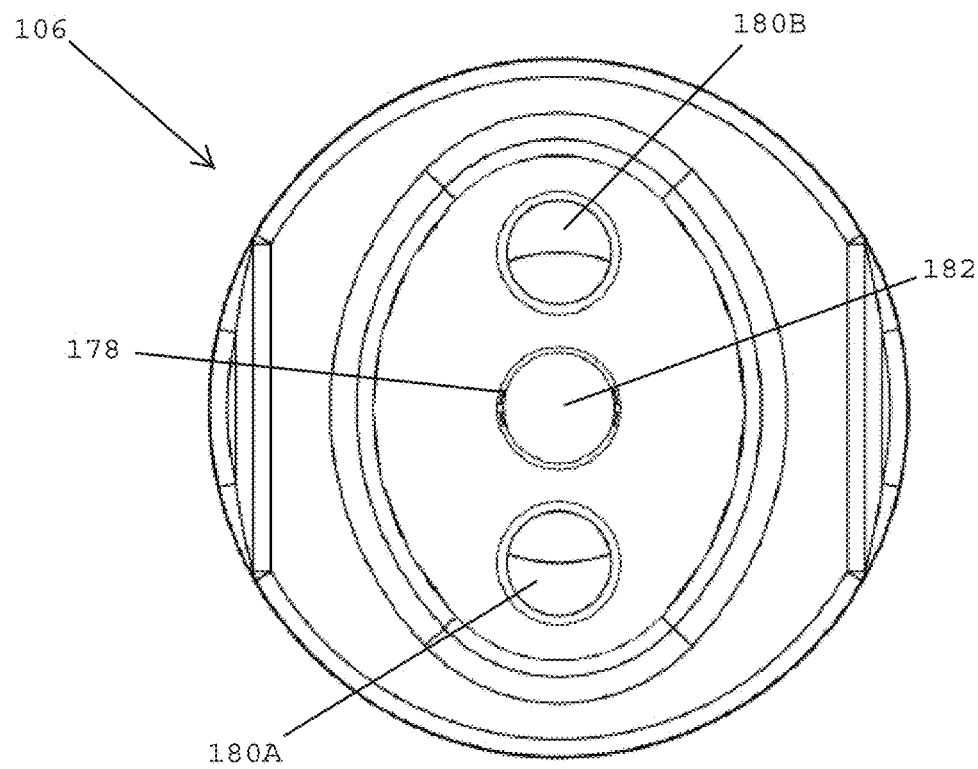
FIG. 13A is a cross-sectional view of the mixing and spraying assembly shown in FIG. 7.
Figure 13B:
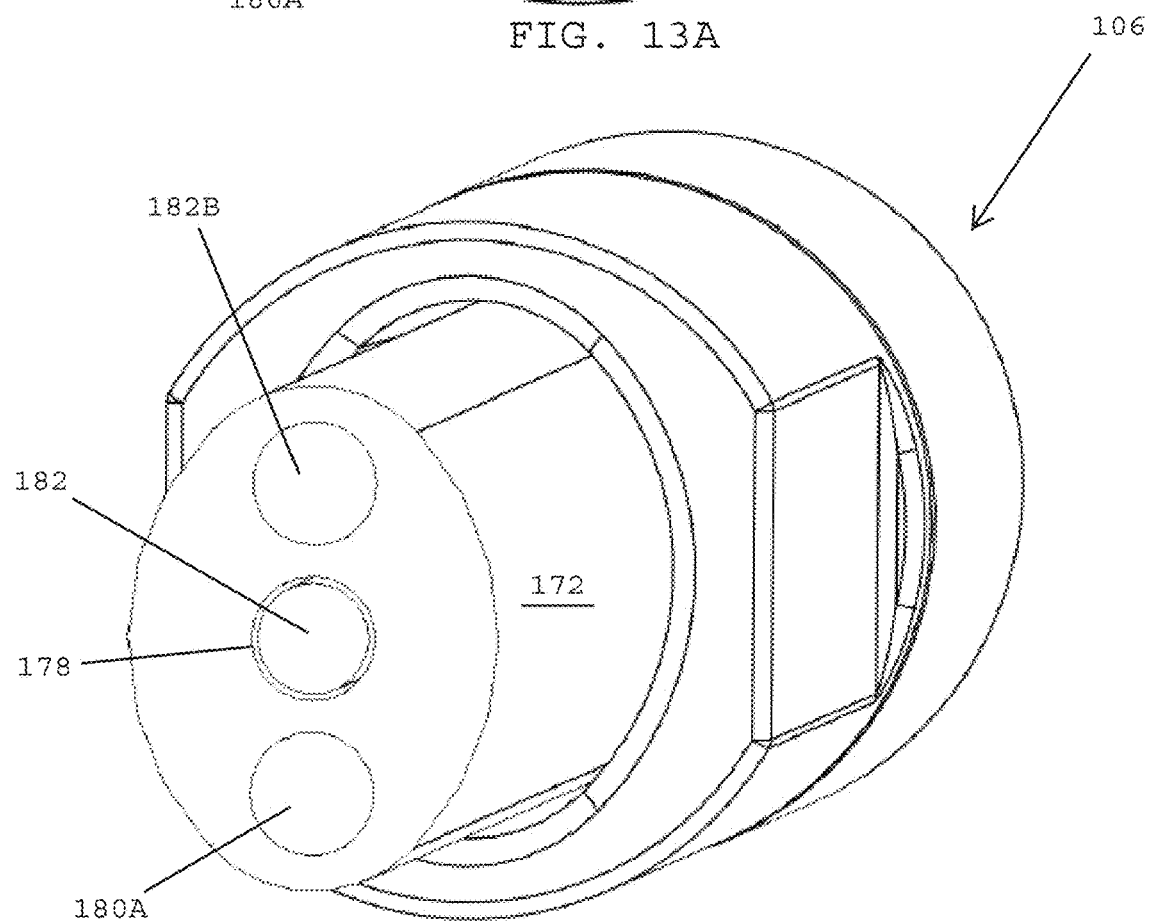
FIG. 13B is a perspective, cross-sectional view of the mixing and spraying assembly shown in FIG. 7.

Referring to FIGS. 13A and 13B, in one embodiment, the flexible shaft 172 of the malleable section 110 (FIG. 1) preferably includes the malleable wire conduit 178 that receives the malleable wire 182. The flexible shaft 172 desirably includes the first and second tissue sealant conduits 180A, 180B that deliver the mixture of the first and second liquids (i.e., the flowable tissue sealant) to the spray tip assembly 112 (FIG. 7) located at the distal end of the sealant applicator 100 (FIG. 1). In one embodiment, when the tissue sealant flows through the first and second tissue sealant conduits 180A, 180B, the first and second liquids have already been mixed by the mixing element 158 located within the mixer housing 150 (FIG. 12).

Figure 14A:
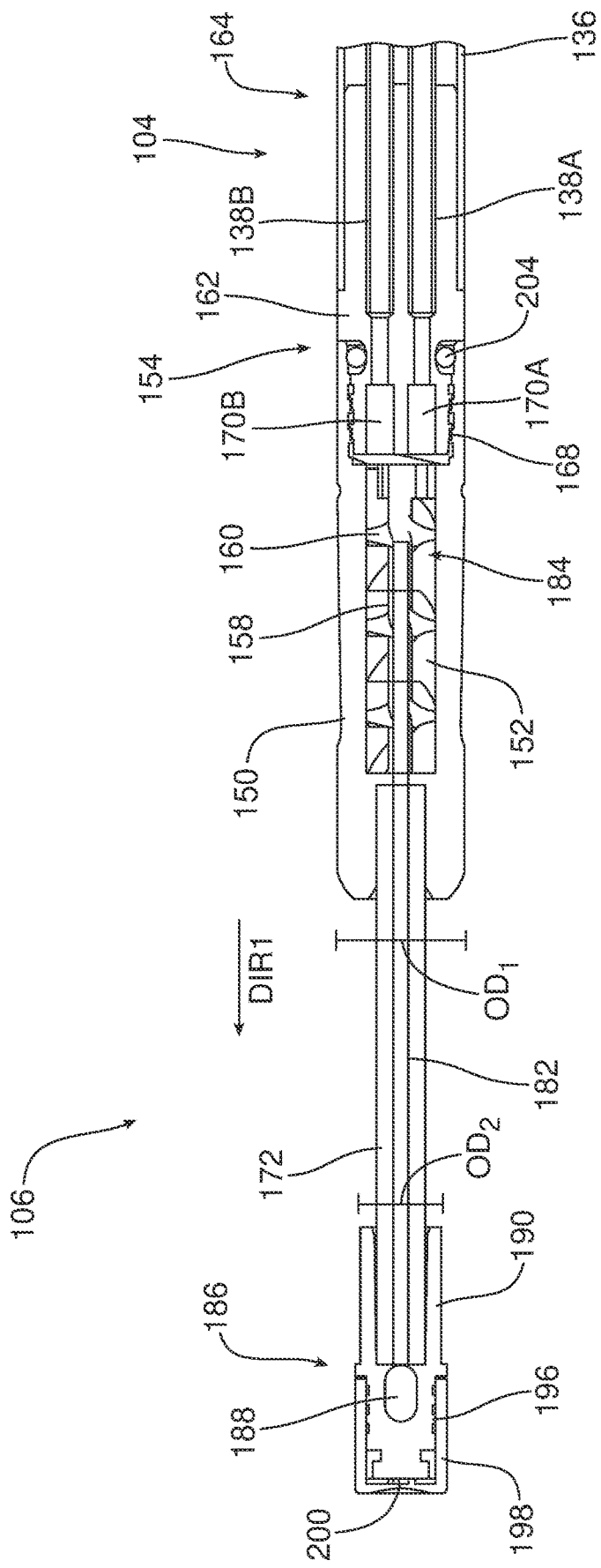
FIG. 14A is a cross-sectional view of the mixing and spraying assembly shown in FIGS. 1 and 7.
Figure 14B:
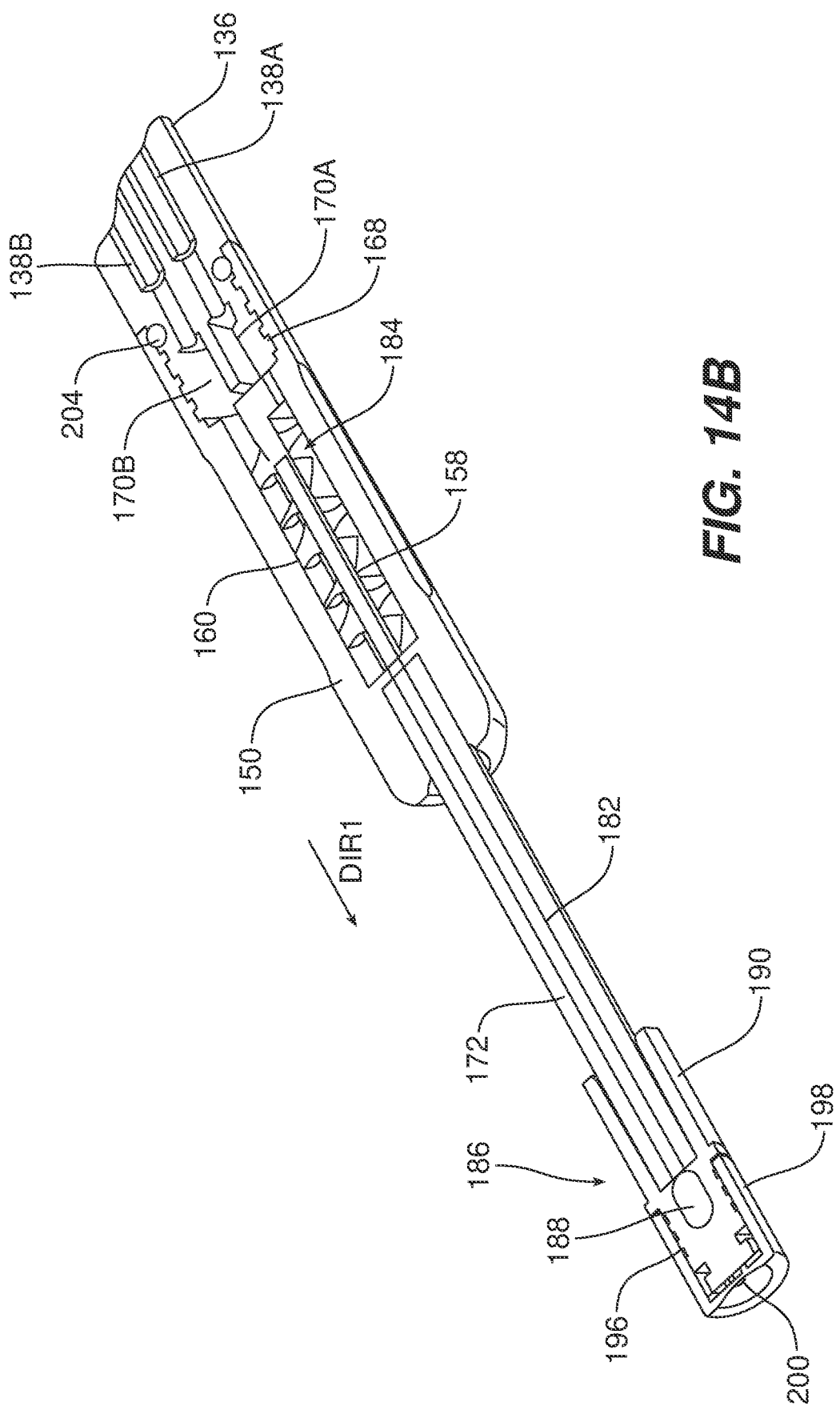
FIG. 14B is a perspective, cross-sectional view of the mixing and spraying assembly shown in FIGS. 1 and 7.

Referring to FIGS. 14A and 14B, in one embodiment, the mixing and spraying assembly 106 is preferably secured to the distal end of the elongated cannula 136 of the sealant delivery assembly 104. In one embodiment, the proximal connector 162 has a proximal end 164 that is inserted into an opening at the distal end of the elongated cannula 136 of the sealant delivery assembly 104. The proximal connector 162 has a first fluid pathway 170A that is in fluid communication with the first flexible tube 138A. The proximal connector 162 also desirably includes a second fluid pathway 170B that is in fluid communication with a distal end of the second flexible tube 138B. The distal end of the proximal connector 162 desirably has external threads 168 that mesh with internal threads at the proximal end 154 of the mixer housing 150 for securing the proximal end of the mixer housing with the distal end of the proximal connector 162. An O-ring 202 may be disposed between an outer surface of the proximal connector 162 and an inner surface of the mixer housing 154 forming a fluid-tight seal therebetween.

In one embodiment, the mixing element 158 is disposed within the elongated conduit 152 of the mixer housing 150. The mixing element 158 preferably has mixing fins 160 that project outwardly from a central shaft of the mixing element. The proximal end 184 of the malleable wire 182 is inserted into the blind hole 202 (FIG. 12) of the mixing element for securing the proximal end of the malleable wire to the mixing element 158. The malleable wire 182 extends through the malleable wire conduit 178 (FIG. 12) of the flexible shaft 172. In one embodiment, the blind hole that is formed in the central shaft of the mixing element 158 extends about ½ to ¾ of the length of the mixing element. In one embodiment, the proximal end of the malleable wire 182 is fully inserted into the blind hole of the center shaft of the mixing element to ensure a reliable connection between the malleable wire and the mixing element. The malleable wire 182 has a distal end 186 with the paddle-shaped attached flange 188 (e.g., an attachment tab) that is connected with the distal connector 190 of the spray tip assembly 112. The spray cup 198 is preferably threaded onto the external threads 196 (FIG. 9A) of the distal connector 190.

In one embodiment, the first fluid from the first syringe barrel 142A (FIG. 4B) is delivered to the mixing and spraying assembly 106 via the first flexible tube 138A and the second fluid from the second syringe barrel 142B (FIG. 4B) is delivered to the mixing and spraying assembly via the second flexible tube 138B. Upon reaching the proximal connector 162 of the mixing and spraying assembly 106, the first and second fluids are desirably directed through the first and second fluid paths 170A, 170B and into the opening at the proximal end of the mixer housing 150. In one embodiment, the first and second fluids are preferably mixed together by the mixing fins 160 as the fluids flow in the distal direction DIR1 along the length of the mixing element 158. In one embodiment, after the first and second fluids have been mixed together by the mixing element 158, the mixed solution is directed through the first and second tissue sealant conduits 180A, 180B (FIG. 12) that extend along the length of the flexible shaft 172. The mixed tissue sealant flows downstream through the first and second tissue sealant conduits 180A, 180B until being directed through the distal connector 190 and into the spray cup 198 for being expressed via the dispensing opening 200 located at a distal end of the spray cup 198. In other embodiments, the flexible shaft may have more than two tissue sealant conduits extending therethrough.

Figure 15:
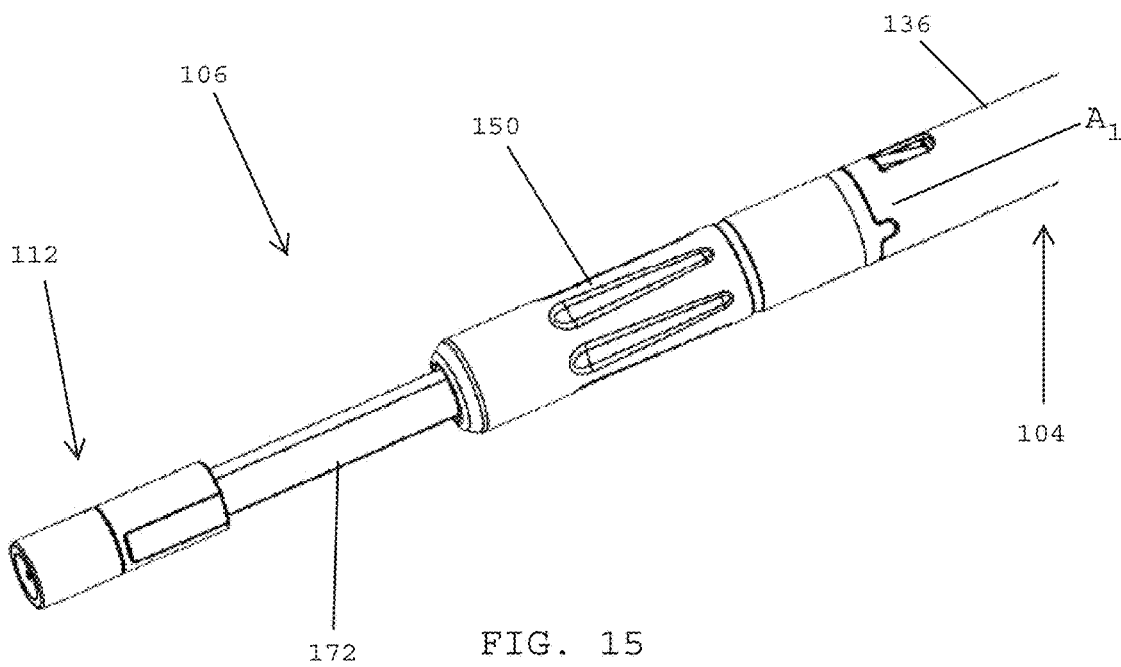
FIG. 15 is a perspective view of the mixing and spraying assembly shown in FIGS. 1 and 7, the mixing and spraying assembly being in a straight configuration and including a mixing assembly, a malleable section, and a spray tip assembly.

Referring to FIG. 15, in one embodiment, the spray tip assembly 112 of the mixing and spraying assembly 106 may be angulated relative to the longitudinal axis $A_1$ of the elongated cannula 136 of the sealant delivery assembly 104. As a result, a surgeon may change the orientation of the spray tip 112 relative to the longitudinal axis $A_1$ of the elongated cannula 136 to access hard to reach locations within a surgical site. In one embodiment, the flexible shaft 172 enables the orientation of the spray tip 112 to be adjusted relative to the orientation or axis of the mixer housing 150 and the elongated cannula 136. When a surgeon bends the flexible shaft for angulating the spray tip assembly relative to the axis of the cannula, the malleable wire that extends through the flexible shaft maintains the bent shape of the flexible shaft that was established by the surgeon.

Figure 16:
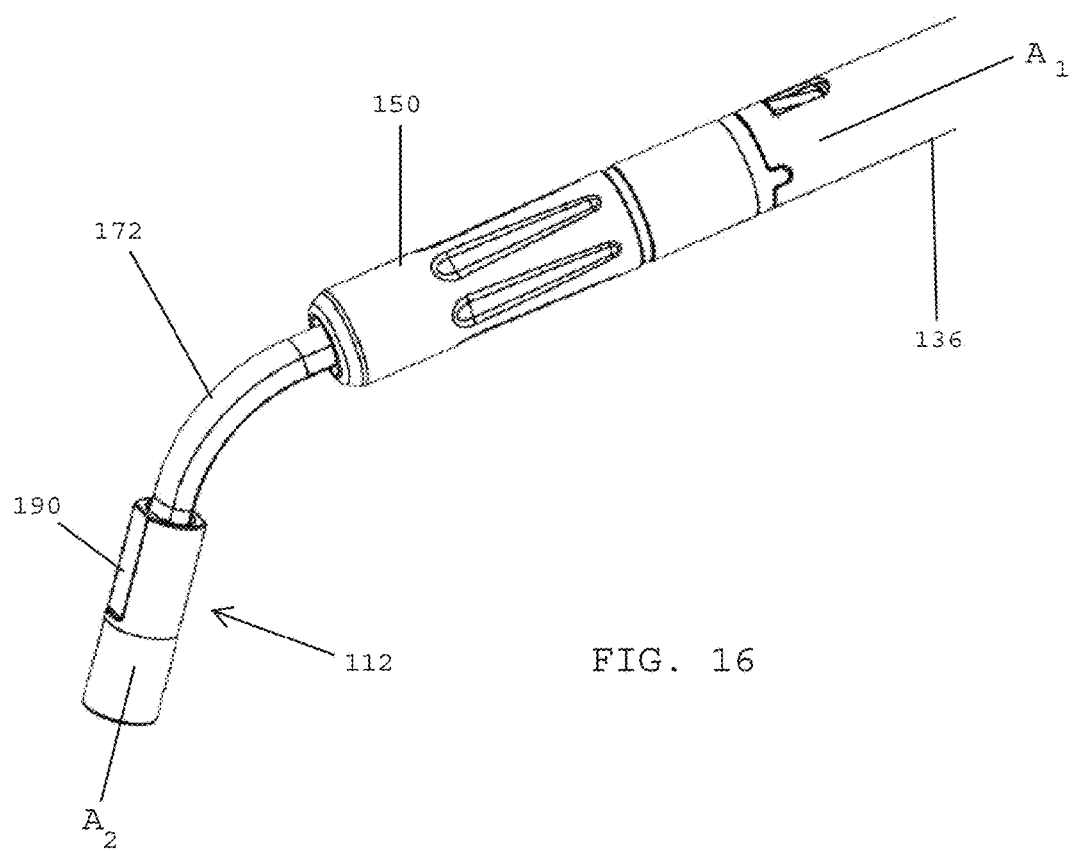
FIG. 16 is a perspective view of the mixing and spraying assembly of FIG. 15 with the malleable section in a bent configuration so that the spray tip assembly is angulated relative to the mixing assembly.

Referring to FIG. 16, in one embodiment, the flexible shaft 172 may be bent so that the spray tip assembly 112 extends along an axis $A_2$ that forms an angle relative to the longitudinal axis $A_1$ of the mixer housing 150 and/or the elongated cannula 136. The flexible shaft 172 preferably contains the malleable wire 182 (FIG. 14A) that holds the spray tip assembly 112 in the angulated orientation shown in FIG. 16. The malleable wire may have shape memory properties for maintaining the orientation of the spray tip assembly that has been selected by a surgeon. The orientation of the spray tip assembly 112 may be adjusted to a different angle than what is shown in FIG. 16 by grasping the distal connector 190 and/or the spray cup 198 to change the orientation of the spray tip assembly 112 relative to the longitudinal axis $A_1$ of the mixer housing 150 and/or the elongated cannula 136. Although the present patent application is not limited by any particular theory of operation, it is believed that placing the mixing element 158 (FIG. 14A) within the mixer housing 150 and positioning the mixer housing 150 at a location that is proximal to the flexible shaft 172 will enable the spray tip assembly 112 to have a shorter length and/or a smaller diameter (than the diameter of the mixer housing), which will enable surgeons to reach narrower locations and/or smaller cavities within a patient and position the spray tip assembly 112 at more acute angles relative to the elongated cannula than is possible when using conventional spray tip assemblies.

Figure 17:
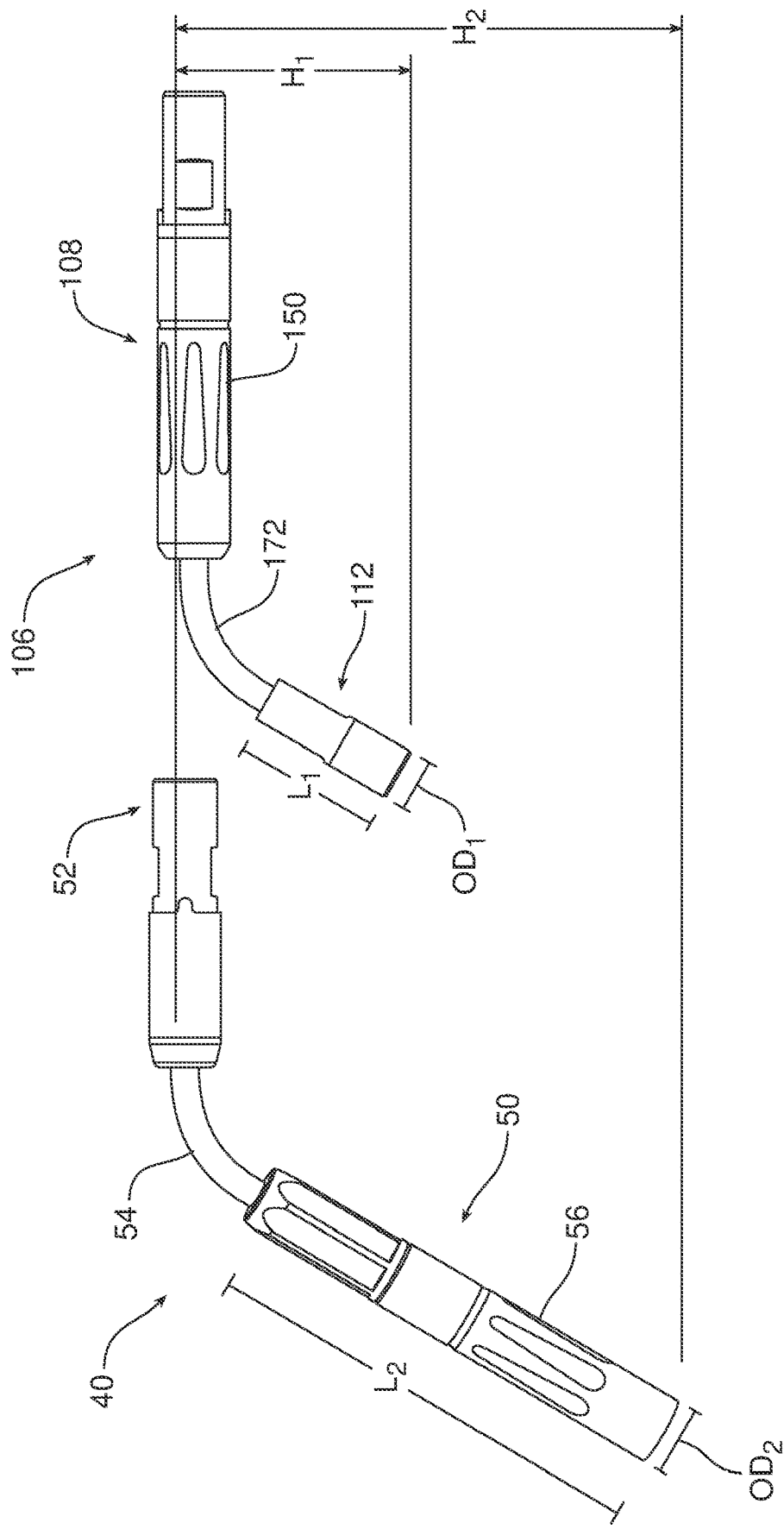
FIG. 17 is a side-by-side view of a conventional spray tip versus the mixing and spraying assembly shown in FIG. 16.

FIG. 17 shows a side-by-side comparison of the mixing and spraying assembly 106 of the present patent application versus a conventional spray tip assembly 50. In the mixing and spraying assembly 106 of the present patent application, the flexible shaft 172 of the malleable section 110 is disposed between the mixer housing 150 and the spray tip assembly 112. As a result, the mixer housing 150 that contains the mixing element 158 (FIG. 14A) is located upstream of the flexible shaft 172, which enables the spray tip assembly 112 to have a shorter length $L_1$. In one embodiment, the length $L_1$ is about 15 mm. In contrast, in the conventional spray device 40, the spray tip assembly 50 includes the mixer housing 56, and the mixer housing is located distal (i.e., downstream) to the distal end of the flexible shaft 54. Because the conventional spray tip 50 includes the mixer housing 56, the length $L_2$ of the convention spray tip assembly is about 35 mm, which is more than twice as long as the shorter length $L_1$ of the spray tip assembly 112 disclosed in the present patent application. Moreover, because the mixing assembly is not directly connected with the spray tip assembly, the spray tip assembly 112 disclosed is the present patent application has a first outer diameter $OD_1$ that is smaller than the second outer diameter $OD_2$ of the mixer housing and the conventional spray tip 50.

A user can manipulate the conventional spray tip 50 to a desired angle for sealant application. As noted above, the spray tip 50 has a distal length $L_2$ of about 35 mm, which may be too long for the spray tip to be used in a narrow space such as a thoracic cavity.

In the present patent application, moving the mixing assembly 108 to the proximal end of an exchangeable mixing and spray tip assembly 106 preferably reduces the diameter of the distal end of the spray tip assembly 112 for improved targeting application, and reduces the length $L_1$ of the spray tip assembly 112 to be less than 15 mm for improved accessibility.

Moreover, due to its shorter length (i.e., 15 mm v. 35 mm), the minimum ceiling space requirement $H_1$ for the spray tip assembly 112 disclosed in the present patent application is less than the minimum ceiling space requirement $H_2$ for the conventional spray tip design 40.

Figure 18:
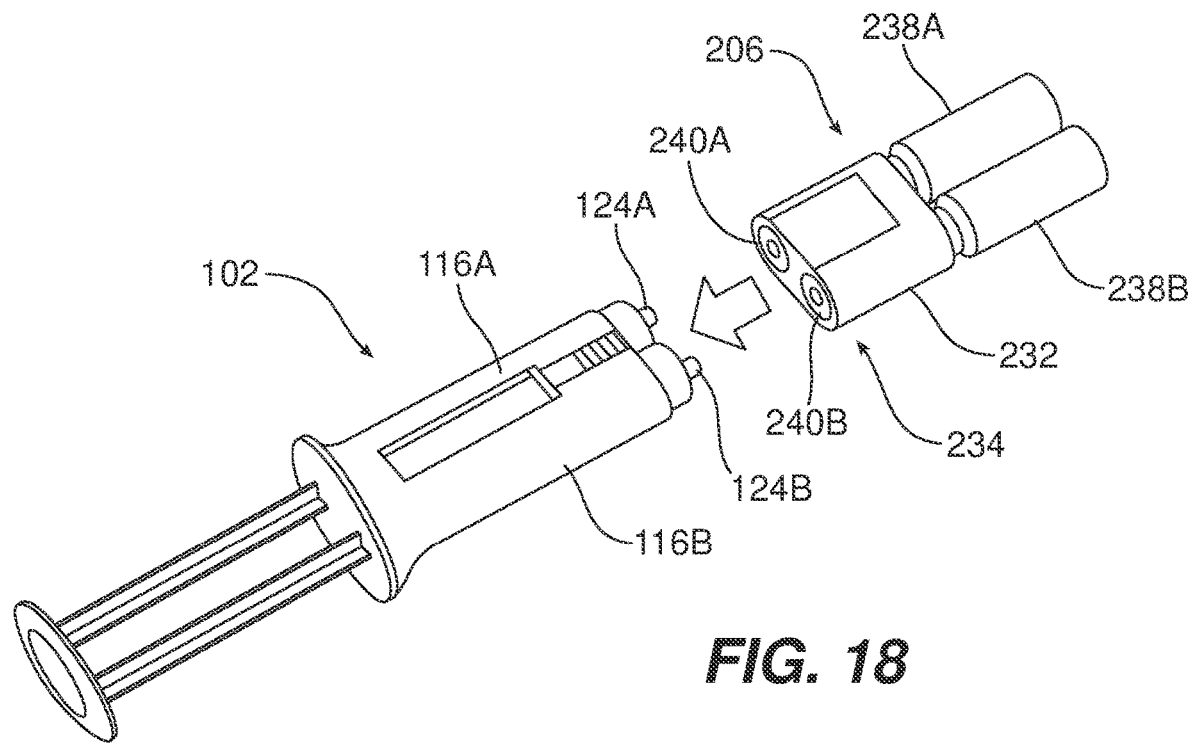
FIG. 18 illustrates a first stage of a method of connecting a vial assembly with a distal end of the syringe assembly shown in FIGS. 1 and 2.

Referring to FIG. 18, in one embodiment, the syringe assembly 102 may be assembled with a vial assembly 206 having a vial assembly housing 232, a first vial 238A that contains a first powdered reactive component, a second vial 238B that contains a second powdered reactive component, a first piercing element 240A, and a second piercing element 240A, as disclosed in commonly assigned U.S. patent application Ser. No. 17/710,094, filed on even date herewith, the disclosure of which is hereby incorporated by reference herein. In one embodiment, after first and second end caps have been removed from the distal end of the syringe assembly 102 to expose the first and second applicator tips 124A, 124B, the distal end of the syringe assembly 102 may be coupled with a proximal end 234 of the vial assembly housing 232 of the vial assembly 206. The first dispensing tip 124A is preferably inserted into a first central opening (e.g., a port) located at the proximal end of the first piercing element 240A and the second dispensing tip 124B is preferably inserted into a second central opening (e.g., a port) located at the proximal end of a second piercing element 240B.

Figure 19:
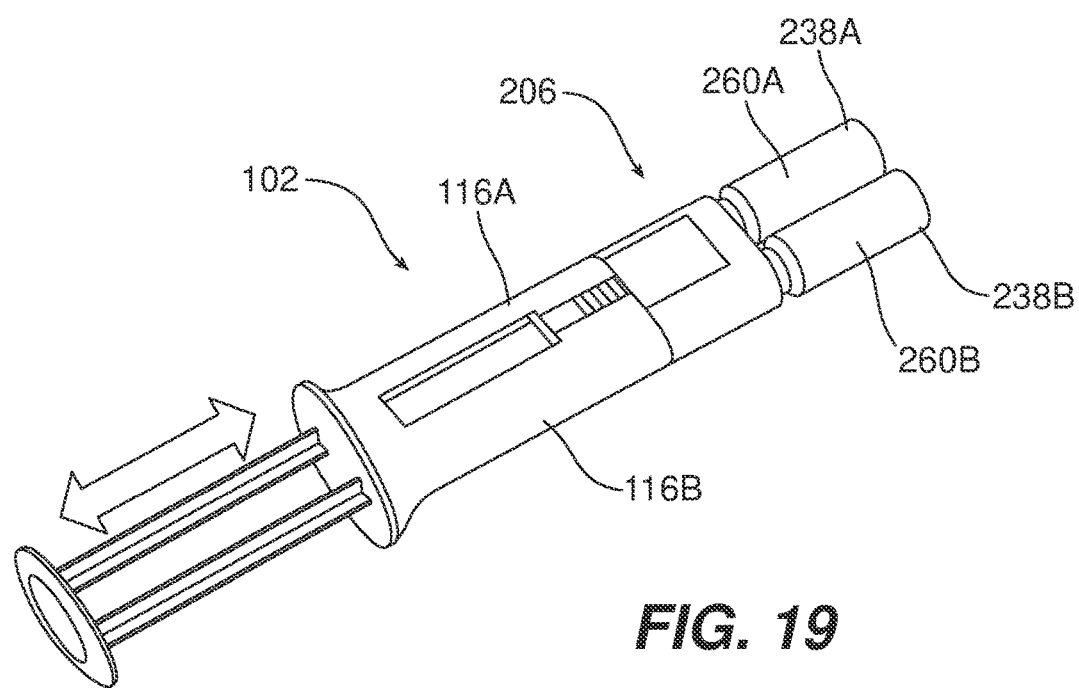
FIG. 19 shows the vial assembly and the syringe assembly of FIG. 18 after the proximal end of the vial assembly has been connected with the distal end of the syringe assembly.

Referring to FIG. 19, after the vial assembly 206 has been assembled with the distal end of the syringe assembly 102, the first fluid disposed within the first syringe barrel 116A of the syringe assembly 102 is preferably in fluid communication with a first powder (e.g., a powdered reactive component) disposed within a first powder chamber 260A of the first vial 238A. Similarly, the second fluid disposed within the second syringe barrel 116B of the syringe assembly 102 is preferably in fluid communication with a second powder (e.g., a powdered reactive component) disposed within the second powder chamber 260B of the second vial 238B.

FIG. 20 shows the distal end of the syringe assembly 102 connected with the proximal end of the vial assembly 206. In one embodiment, the first and second piercing elements 240A, 240B may be extended for piercing sealing membranes 248A, 248B that close vial openings at proximal ends of the respective first and second vials 238A, 238B. The syringe assembly includes the first syringe barrel 116A having a first fluid chamber 142A that contains a first fluid that is used for reconstituting the first powder within the first powder chamber 260A of the first vial 238A. The syringe assembly 102 also desirably includes the second syringe barrel 116B having the second fluid chamber 142B that contains a second fluid that is used for reconstituting the second powder within the second powder chamber 260B of the second vial 238B. The first syringe barrel 116A is connected with the proximal end of the vial assembly 206 so that the first dispensing tip 124A of the first syringe barrel 116A is aligned with and in fluid communication with a first vial opening 246A of the first vial 238A. The first vial 238A has the first powder chamber 160A that contains a first powder, which will be reconstituted using the first fluid disposed within the first fluid chamber 142A of the first syringe barrel 116A. The second dispensing tip 124B at the distal end of the second syringe barrel 116B is preferably in alignment with the second vial opening 246B of the second vial 238B. The second vial 238B preferably includes the second powder chamber 260B that contains a second powder, which will be reconstituted using the second fluid disposed within the second fluid chamber 142B of the second syringe barrel 116B.

During the stage shown in FIG. 20, the first fluid and the first powder remain isolated from the second fluid and the second powder.

In one embodiment, the first fluid within the fluid chamber 142A of the first syringe 116A is mixed with the first powder in the first vial 238A by advancing and retracting the dual barrel plunger 118 in distal directions DIR1 and proximal directions DIR2. As the first plunger rod 120A is advanced toward the distal end of the syringe assembly 114, the first fluid within the first fluid chamber 142A of the first syringe 116A is forced into the first powder chamber 260A of the first vial 238A for reconstituting the first powder into a first therapeutic solution. When the first plunger rod 120 is retracted away from the distal end of the syringe assembly 102, the first therapeutic solution (i.e., a mixture of the first powder and the first fluid) is drawn back into the first fluid chamber 142A of the first syringe 116A. The first plunger rod 120A may be repeatedly reciprocated back and forth between an extended position and a retracted position for thoroughly mixing the first fluid and the first powder to form the first precursor solution (e.g., a first fluid; a first solution). In one embodiment, after the first precursor solution has been formed, the first plunger rod 120A is preferably fully retracted for drawing the entire volume of the first precursor solution back into the first fluid chamber 142A of the first syringe 116A.

In one embodiment, the second fluid within the second fluid chamber 142B of the second syringe 116B is mixed with the second powder within the second vial 238B by advancing and retracting the dual barrel plunger 118 in distal directions DIR1 and proximal directions DIR2. As the second plunger rod 120B is advanced toward the distal end of the syringe assembly 102 (i.e., in direction DIR1), the second fluid within the second fluid chamber 142B of the second syringe 116B is forced into the second powder chamber 260B of the second vial 238B for reconstituting the second powder into a second therapeutic solution. When the second plunger rod 120B is retracted away from the distal end of the syringe assembly 102 (i.e., in the direction DIR2), the second therapeutic solution (i.e., a mixture of the second powder and the second fluid) is drawn back into the second fluid chamber 142B of the second syringe 116B. The second plunger rod 120B may be repeatedly reciprocated back and forth between an extended position and a retracted position for thoroughly mixing the second fluid and the second powder to form the second precursor solution (e.g., a flowable fluid). In one embodiment, after the second precursor solution has been formed, the second plunger rod 120B is preferably fully retracted for drawing the entire volume of the second precursor solution into the second fluid chamber 142B of the second syringe 116B.

Referring to FIGS. 1 and 20, in one embodiment, after the first and second precursor solutions have been generated and drawn back into the first and second fluid chambers 142A, 142B of the respective first and second syringes 116A, 116B of the syringe assembly 102, the vial assembly 206 may be uncoupled from the distal end of the syringe assembly 102, whereupon the sealant delivery assembly 104 may be secured to the distal end of the syringe assembly 102 for expressing a mixture of the first and second precursor solutions (i.e., the tissue sealant) from the spray tip assembly 112 located at the distal end of the sealant applicator 100. In one embodiment, the sealant delivery assembly housing 128 at the proximal end of the sealant delivery assembly 104 is preferably connected with the distal end of the syringe assembly 102. The cannula 136 preferably extends toward the distal end of the sealant delivery assembly 104.

After the sealant delivery assembly 104 has been secured to the distal end of the syringe assembly 102, the first fluid chamber 142A of the first syringe 116A that contains the first precursor solution is preferably in fluid communication with the mixing and spraying assembly 106 via the first flexible tube 138A (FIG. 4B) that extends through the elongated cannula 136. The second fluid chamber 142B of the second syringe 116B that contains the second precursor solution is preferably in fluid communication with the mixing and spraying assembly 106 via the second flexible tube 138B (FIG. 4B) that extends through the elongated cannula 136.

In one embodiment, the dual barrel plunger 118 is depressed in the distal direction designated DIR1 to force the first and second precursor solutions from the first and second fluid chambers 142A, 142B of the respective first and second syringes 116A, 116B, whereupon the first and second precursor solutions flow through the respective first and second flexible tubes 138A, 138B (FIG. 4A) until they reach the mixing and spraying assembly 106. Upon reaching the mixing and spraying assembly 106, the first and second precursor solutions are mixed together by the mixing element 158 (FIG. 14A) located within the mixer housing 108, whereupon the first and second precursor solutions react with one another to form a tissue sealant or hemostat, which passes through the malleable section 110 for being expressed from the dispensing opening 200 of the spray cup 198 (FIG. 14A) located at the distal end of the spray tip assembly 112 of the mixing and spraying assembly 106.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A mixing and spraying assembly for a tissue sealant comprising:
    a mixing assembly located at a proximal end of said mixing and spraying assembly;
    a spray tip assembly located at a distal end of said mixing and spraying assembly; and
    a malleable section having a proximal end connected with said mixing assembly and a distal end connected with said spray tip assembly for enabling said spray tip assembly to be angulated relative to said mixing assembly, the malleable section comprising a flexible shaft having a proximal end, distal end, and a length that extends between the proximal and distal ends thereof,
    said malleable section further comprising:
        a malleable wire conduit that extends along the length of said flexible shaft; and
        a malleable wire disposed in said malleable wire conduit of said flexible shaft, said malleable wire having a length that is greater than the length of said flexible shaft, wherein said malleable wire has a proximal end that extends beyond the proximal end of said flexible shaft and that is connected to said mixing assembly and a distal end that extends beyond the distal end of said flexible shaft and that is connected to said spray tip assembly,
    wherein the mixing assembly comprises:
        a mixer housing having a proximal end, a distal end and a mixer housing conduit extending along a length of said mixer housing from the proximal end to the distal end of said mixer housing; and
        a mixing element disposed within said mixer housing conduit, wherein the proximal end of said malleable wire that extends beyond the proximal end of said flexible shaft is secured to said mixing element,
    wherein said mixing element comprises:
        a static mixer having a center shaft that extends along a length of said static mixer, said center shaft of said static mixer having a proximal end and a distal end, and said static mixer having a plurality of mixing fins that are spaced from one another along the length of said static mixer; and
        a blind hole formed in said center shaft of said static mixer that extends from the distal end of said center shaft toward the proximal end of said center shaft, the proximal end of said malleable wire being disposed in said blind hole formed in said center shaft of said static mixer for connecting the proximal end of said malleable wire to said static mixer.

2. The mixing and spraying assembly as claimed in claim 1, wherein said mixing assembly further comprises:
    a proximal connector having a proximal end that is configured for being inserted into an opening at a distal end of an elongated cannula of a sealant applicator and a distal end having external threads; and
    said mixer housing having internal threads located at the proximal end of said mixer housing that are configured to mesh with said external threads at the distal end of said proximal connector for securing said mixer housing to said proximal connector.

3. The mixing and spraying assembly as claimed in claim 2, wherein said proximal connector comprises:

a first fluid pathway extending from the proximal end to the distal end of said proximal connector, wherein said first fluid pathway is in fluid communication with the proximal end of said static mixer;

a second fluid pathway extending from the proximal end to the distal end of said proximal connector, wherein said second fluid pathway is in fluid communication with the proximal end of said static mixer;

a first flexible tube disposed in said first fluid pathway of said proximal connector for supplying a first fluid to the proximal end of said mixer housing; and a second flexible tube disposed in said second fluid pathway of said proximal connector for supplying a second fluid to the proximal end of said mixer housing.

4. The mixing and spraying assembly as claimed in claim 3, wherein said static mixer is adapted for mixing said first and second fluids, whereupon said first and second fluids react together to form a tissue sealant.

5. The mixing and spraying assembly as claimed in claim 4, wherein said flexible shaft of said malleable section comprises one or more tissue sealant conduits extending along the length thereof for supplying said tissue sealant to said spray tip assembly.

6. The mixing and spraying assembly as claimed in claim 5, wherein said malleable wire conduit extends along a central axis of said flexible shaft, and wherein said one or more tissue sealant conduits of said flexible shaft comprise first and second tissue sealant conduits that extend along opposite sides of said malleable wire conduit.

7. The mixing and spraying assembly as claimed in claim 6, wherein said spray tip assembly comprises:
a distal connector having a proximal end and a distal end having external threads; the proximal end of said distal connector having a central opening that seats the distal end of said flexible shaft, the distal end of said malleable wire that extends beyond the distal end of said flexible shaft being connected with said distal connector; and
a spray cup having a spray opening for expressing said tissue sealant that is supplied through said first and second tissue sealant conduits of said flexible shaft, said spray cup having a tube-shaped proximal end with internal threads that are configured to mesh with the external threads at the distal end of said distal connector for securing said spray cup to said distal connector.

8. The mixing and spraying assembly as claimed in claim 7, wherein the distal end of said malleable wire that is secured to said distal connector of said spray tip assembly comprises a paddle-shaped flange having a width that is greater than the diameter of a section of said malleable wire that extends to the proximal end of said malleable wire.

9. A mixing and spraying assembly for expressing a tissue sealant comprising:
a mixing assembly that is configured for mixing first and second fluids that chemically react together to form a tissue sealant;
a spray tip assembly configured for expressing said tissue sealant; and
a malleable section having a proximal end connected with said mixing assembly and a distal end connected with said spray tip assembly for enabling said spray tip assembly to be angulated relative to said mixing assembly, wherein said malleable section has one or more tissue sealant conduits extending along a length thereof for delivering said tissue sealant from said mixing assembly to said spray tip assembly,
wherein said malleable section comprises:
a flexible shaft having a malleable wire conduit extending from the proximal end to the distal end thereof; and
a malleable wire disposed within said malleable wire conduit, said malleable wire having a proximal end that extends beyond the proximal end of said flexible shaft for being connected to said mixing assembly and a distal end that extends beyond the distal end of said flexible shaft for being connected to said spray tip assembly,
wherein said mixing assembly comprises:
a mixer housing having a proximal end, a distal end, and a mixer housing conduit extending from the proximal end to the distal end of said mixer housing;
a mixing element disposed within said mixer housing conduit of said mixer housing;
wherein said spray tip assembly comprises a distal connector coupled with the distal end of said flexible shaft and a spray cup having a spray opening secured to a distal end of said distal connector; and
wherein said proximal end of said malleable wire is secured to said mixing element disposed within said mixer housing and the distal end of said malleable wire being secured to said distal connector of said spray tip assembly, and
wherein said mixing element comprises:
a static mixer having a center shaft that extends along a length of said static mixer, said center shaft of said static mixer having a proximal end and a distal end, said static mixer having a plurality of mixing fins that are spaced from one another along the length of said static mixer; and
a blind hole formed in said center shaft of said static mixer that extends from the distal end of said center shaft toward the proximal end of said center shaft, wherein the proximal end of said malleable wire is disposed in said blind hole formed in said center shaft of said static mixer for connecting the proximal end of said malleable wire to said static mixer.

10. The mixing and spraying assembly as claimed in claim 9, wherein said mixer housing has a longitudinal axis that extends from the proximal end to the distal end of said mixer housing, and wherein said malleable section enables said spray tip assembly to be angulated relative to the longitudinal axis of said mixer housing.

11. The mixing and spraying assembly as claimed in claim 9, wherein said mixer housing has a first outer diameter and said spray tip assembly has a second outer diameter that is less than the first outer diameter of said mixer housing.

12. A method of expressing a tissue sealant comprising:
obtaining a mixing and spraying assembly including a mixing assembly, a spray tip assembly, and a malleable section having a proximal end connected with said mixing assembly and a distal end connected with said spray tip assembly for spacing said spray tip assembly away from said mixing assembly and for enabling said spray tip assembly to be angulated relative to said mixing assembly;
directing first and second fluids into the proximal end of said mixing assembly;
mixing said first and second fluids within said mixing assembly whereupon said first and second fluids react together to form a tissue sealant; and
passing said tissue sealant through one or more tissue sealant conduits that extend through said malleable section to supply said tissue sealant to said spray tip assembly; expressing said tissue sealant from a distal end of said spray tip assembly, wherein said malleable section comprises:
- a flexible shaft having a malleable wire conduit extending from the proximal end to the distal end thereof; and
- a malleable wire disposed within said malleable wire conduit, said malleable wire having a proximal end that extends beyond the proximal end of said flexible shaft for being connected to said mixing assembly and a distal end that extends beyond the distal end of said flexible shaft, the proximal end of said malleable wire being connected to said mixing assembly and the distal end of said malleable wire being connected to said spray tip assembly, wherein said mixing assembly comprises:
- a mixer housing having a proximal end, a distal end, and a mixer housing conduit extending from the proximal end to the distal end of said mixer housing;
- a mixing element disposed within said mixer housing conduit of said mixer housing;

wherein said spray tip assembly comprises a distal connector coupled with the distal end of said flexible shaft and a spray cup having a spray opening secured to a distal end of said distal connector; and wherein said mixing element comprises:
- a static mixer having a center shaft that extends along a length of said static mixer, said center shaft of said static mixer having a proximal end and a distal end, said static mixer having a plurality of mixing fins that are spaced from one another along the length of said static mixer; and
- a blind hole formed in said center shaft of said static mixer that extends from the distal end of said center shaft toward the proximal end of said center shaft, wherein the proximal end of said malleable wire is disposed in said blind hole formed in said center shaft of said static mixer for connecting the proximal end of said malleable wire to said static mixer.

13. The method as claimed in claim 12, wherein said first fluid comprises Fibrinogen and said second fluid comprises Thrombin that reacts with said Fibrinogen for forming said tissue sealant.

* * * * *